(12) United States Patent
Daifuku et al.

(10) Patent No.: US 7,589,092 B2
(45) Date of Patent: *Sep. 15, 2009

(54) PRODRUGS OF HETEROARYL COMPOUNDS

(75) Inventors: Richard Daifuku, Mercer Island, WA (US); Alexander Gall, Woodinville, WA (US); Dmitri Sergueev, Bothell, WA (US); Dina Sologub, Kirkland, WA (US); Kevin Harris, Bothell, WA (US)

(73) Assignee: Koronis Pharmaceuticals, Incorporated, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/616,646

(22) Filed: Dec. 27, 2006
(Under 37 CFR 1.47)

(65) Prior Publication Data

US 2008/0249097 A1    Oct. 9, 2008

Related U.S. Application Data

(63) Continuation-in-part of application No. 10/816,161, filed on Mar. 31, 2004, now Pat. No. 7,244,732.

(60) Provisional application No. 60/480,037, filed on Jun. 20, 2003.

(51) Int. Cl.
*A61K 31/53* (2006.01)
*A61K 31/18* (2006.01)
*C07D 251/08* (2006.01)
*C07D 251/10* (2006.01)
*C07D 405/04* (2006.01)

(52) U.S. Cl. .................. 514/241; 514/245; 544/196; 544/197; 544/198; 544/204; 544/205; 544/206; 544/220; 544/221

(58) Field of Classification Search .................. 514/241, 514/245
See application file for complete search history.

(56) References Cited

U.S. PATENT DOCUMENTS 3,101,335 A    8/1963    Francis et al.
4,140,850 A    2/1979    Wierenga
5,705,643 A    1/1998    Reinehr et al.
7,244,732 B2    7/2007    Daifuku et al.

FOREIGN PATENT DOCUMENTS

DE    24 51 899 A1    5/1975
DE    101 41 271 A1    3/2003

OTHER PUBLICATIONS

Anderson, J.P. et al., "Viral Error Catastrophe by Mutagenic Nucleosides," *Annu. Rev. Microbiol.*, 2004, vol. 58, pp. 183-205.
Daifuku, R., "Stealth Nucleotides Mode of Action and Potential Use in the Treatment of Viral Disease," *Biodrugs*, 2003, vol. 17, No. 3, pp. 169-177.
Dovlatyan, V.V. et al., "Synthesis and Hydrolysis of 2-cyanomethoxy-4-N-methyl-N-cyanamino-6-dialkylamino-s-triazines," *Armyanskii Khimicheskii Zhurnal*, 1980, vol. 33, No. 11, pp. 943-946.
Slotta, K.H. et al., "Isocyanates, VI. Condensations of Methyl Isocyanate With Cyanamide Under the Influence of Triethylphosphine," *Berichte der Deutschen Chemischen Gesellschaft (Abteilung) B: Abhandlungen*, 1929, vol. 62B, pp. 137-145.
Vulliet, E. et al., "Simulated Sunlight-Induced Photodegradations of Triasulfuron and Cinosulfuron in Aqueous Solutions," *Journal of Agricultural and Food Chemistry*, 2002, vol. 50, pp. 1081-1088.
Yuan, C. et al., "An Efficient Method for the Preparation of Amidinoureas," *Tetrahedron Letters*, 1996, vol. 37, No. 12, pp. 1945-1948.
Garcia, Ramon Güimil, et al. "Synthesis of Oligonucleotide Inhibitors of DNA (Cytosine-C5) Methyltransferase Containing 5-Azacytosine Residues at Specific Sites," *Antisense & Nucleic Acid Drug Development*, 2001, vol. 11, pp. 369-378.
Samuel, Charles, "Virus-Host Interaction Minireview Series: Human Immunodeficiency Virus, Hepatitis C Virus, and Influenza Virus," *Journal of Biological Chemistry*, 2006, vol. 281, No. 13, pp. 8305-8307.

*Primary Examiner*—Venkataraman Balasubramanian
(74) *Attorney, Agent, or Firm*—Townsend and Townsend and Crew LLP

(57) ABSTRACT

The present invention provides hydrophobic prodrugs of bases, nucleosides, and nucleotides as well as methods of using the prodrugs as antiviral and anti-cancer chemotherapeutic agents.

25 Claims, 2 Drawing Sheets

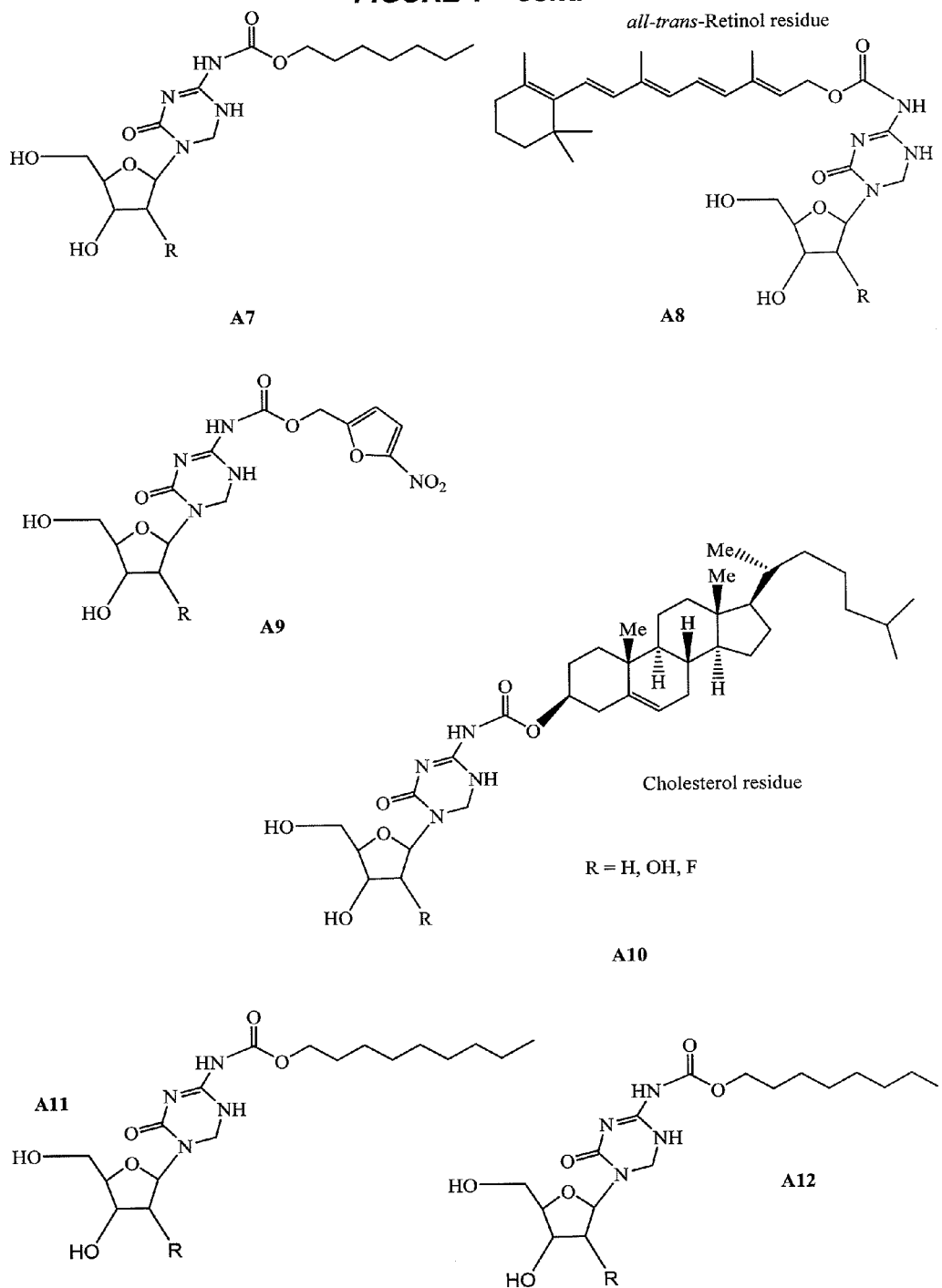
FIGURE 1 – cont.

PRODRUGS OF HETEROARYL COMPOUNDS

CROSS-REFERENCE TO RELATED APPLICATIONS

This application is a Continuation-in-Part of U.S. Ser. No. 10/816,161, filed Mar. 31, 2004, now U.S. Pat. No. 7,244,732, which claims priority to U.S. Provisional Application No. 60/480,037, filed Jun. 20, 2003, each of which is incorporated in its entirety herein.

BACKGROUND OF THE INVENTION

Some of mankind's greatest medical threats are caused by viruses, including AIDS, hepatitis, rhinovirus infections of the respiratory tract, flu, measles, polio and others. There are a number of chronic persistent diseases caused by RNA or DNA viruses, that replicate through a RNA intermediate, which are difficult to treat, such as hepatitis B and C, and HIV. A number of common human diseases are caused by RNA viruses that are replicated by a viral encoded RNA replicase. Included in this group are influenza (Zurcher, et al., *J. Gen. Virol*. 77:1745 (1996)), dengue fever (Becker, *Virus-Genes* 9:33 (1994)), and rhinovirus infections (Horsnell, et al., *J. Gen. Virol*., 76:2549 (1995)). Animals also suffer from a wide variety of RNA viral diseases, including feline leukemia and immunodeficiency, *Visna maedi* of sheep, bovine viral diarrhea, bovine mucosal disease, and bovine leukemia. Although some vaccines are available for DNA viruses, diseases such as hepatitis B are still prevalent. Hepatitis B is caused by a DNA virus that replicates its genome through a RNA intermediate (Summers and Mason, *Cell* 29:4003 (1982)). While an effective vaccine exists as a preventive, treatment for chronic persistent Hepatitis B Viral (HBV) infection only cures a minority of patients.

Chain terminating nucleoside analogs have been used extensively for the treatment of infections by DNA viruses and retroviruses. These analogs have been designed to be incorporated into DNA by DNA polymerases or reverse transcriptases. Once incorporated, they cannot be further extended and thus terminate DNA synthesis. Unfortunately, there is immediate selective pressure for the development of resistance against such chain terminating analogs that results in development of mutations in the viral polymerase that prevent incorporation of the nucleoside analog.

An alternative strategy is to utilize mutagenic deoxyribonucleosides (MDRN) or mutagenic ribonucleosides (MRN) that are preferentially incorporated into a viral genome. MDRN are incorporated into DNA by viral reverse transcriptase or by a DNA polymerase enzyme. MRN are incorporated into viral RNAs by viral RNA replicases. As a result, the mutations in the viral genome affect all viral proteins by creating inactive versions of them. These mutations are perpetuated and accumulated with each viral replication cycle. Eventually, through the sheer number of mutations, a gene which is necessary for the function, replication, or transfection of the virus will be inactivated which will cease the viral life cycle. Because MDRN and MRN are not specifically targeting one particular viral protein, there is less likelihood for the development of resistance.

5-aza-2'-deoxycytidine (5-aza-dC) is an antineoplastic agent that has been tested in patients with leukemia and is thought to act predominantly by demethylating DNA. Methylation is thought to silence tumor growth suppressor and differentiation genes. Interestingly, 5-aza-dC affects other targets. For example, 5-aza-dC was shown to inhibit HIV replication in vitro, although the mechanism of action was not determined (see e.g., Bouchard et al, *Antimicrob. Agents Chemother*. 34:206-209 (2000)). Deamination of 5-aza-dC to 5-aza-2'-deoxyuridine (5-aza-dU) has been shown to result in loss of antineoplastic activity (see e.g., Momparler, et al., *Leukemia*. 11:1-6 (1997)).

While 5-azacytidine (5-aza-C) or 5-aza-dC and variants thereof show promise as MDRNs and MRNs, these compounds are also unstable and rapidly degrade upon reconstitution. For example, at pH 7.0, a 10% degradation in 5-aza-dC occurs at temperatures of 25° C. and 50° C. after 5 and 0.5 hours, respectively (see e.g., Van Groeningen et al., *Cancer Res*. 46:4831-4836 (1986)). Thus, therapeutic use of these compounds is limited for treatment of both viral diseases and cancer. The present invention solves this and other problems.

BRIEF SUMMARY OF THE INVENTION

The present invention provides hydrophobic prodrugs of bases, nucleosides, and nucleotides as well as methods of using the prodrugs as antiviral and anti-cancer chemotherapeutic agents. Thus, in a first aspect, the compounds of the invention have a structure according to Formula I:

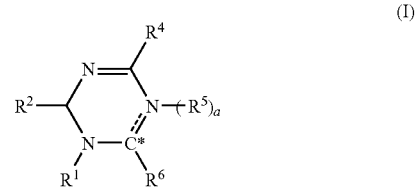

in which a is either 0 or 1. The dashed line represents a double bond between C* and N when a is 0. The symbol $R^2$ is a member selected from (=O) and $NR^7R^8$. $R^4$ is a member selected from H, halogen, $OR^3$, $NR^7R^8$, halogen, nitrile, and substituted and unsubstituted $(C_1-C_5)$alkyl. The symbol $R^6$ is a member selected from H, halogen, $OR^3$, $NR^3R^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl. $R^7$, $R^8$, $R^5$ and $R^1$ are members independently selected from H, $OR^3$, $NR^3R^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl. The symbol $R^3$ is independently selected from H, substituted or unsubstituted alkyl and substituted or unsubstituted acyl. The groups $R^7$ and $R^8$, $R^8$ and $R^5$, and $R^5$ and $R^6$, together with the atoms to which they are joined, optionally form a substituted or unsubstituted 5- to 7-membered ring. In the compounds of the invention, at least one member selected from $R^3$, $R^5$, $R^7$, and $R^8$, alone or together with the atom to which it is covalently bonded, is selected from carbamate and urea linkers.

In a second aspect, the compounds of Formula I are used to treat a viral disease through administering a therapeutically effective amount of the compound to a patient in need of such treatment.

In a third aspect of the present invention, the compounds of Formula I are used to treat cancer through administering a therapeutically effective amount of the compound to a patient in need of such treatment.

In a fourth aspect, the present invention provides a pharmaceutical composition comprising a pharmaceutically acceptable carrier and a compound of Formula I.

In a fifth aspect, the present invention provides a pharmaceutical composition comprising a therapeutically effective amount of a compound of the present invention and an antiviral agent, for treatment of HIV infection.

In a sixth aspect, the present invention provides a method for treating HIV infection, the method comprising the step of administering to a subject in need of such treatment a therapeutically effective amount of a compound of the present invention and an antiviral agent.

These and other aspects, objects and advantages of the present invention will be apparent from the detailed description that follows.

DETAILED DESCRIPTION OF THE INVENTION

I. Introduction

Figure 1:
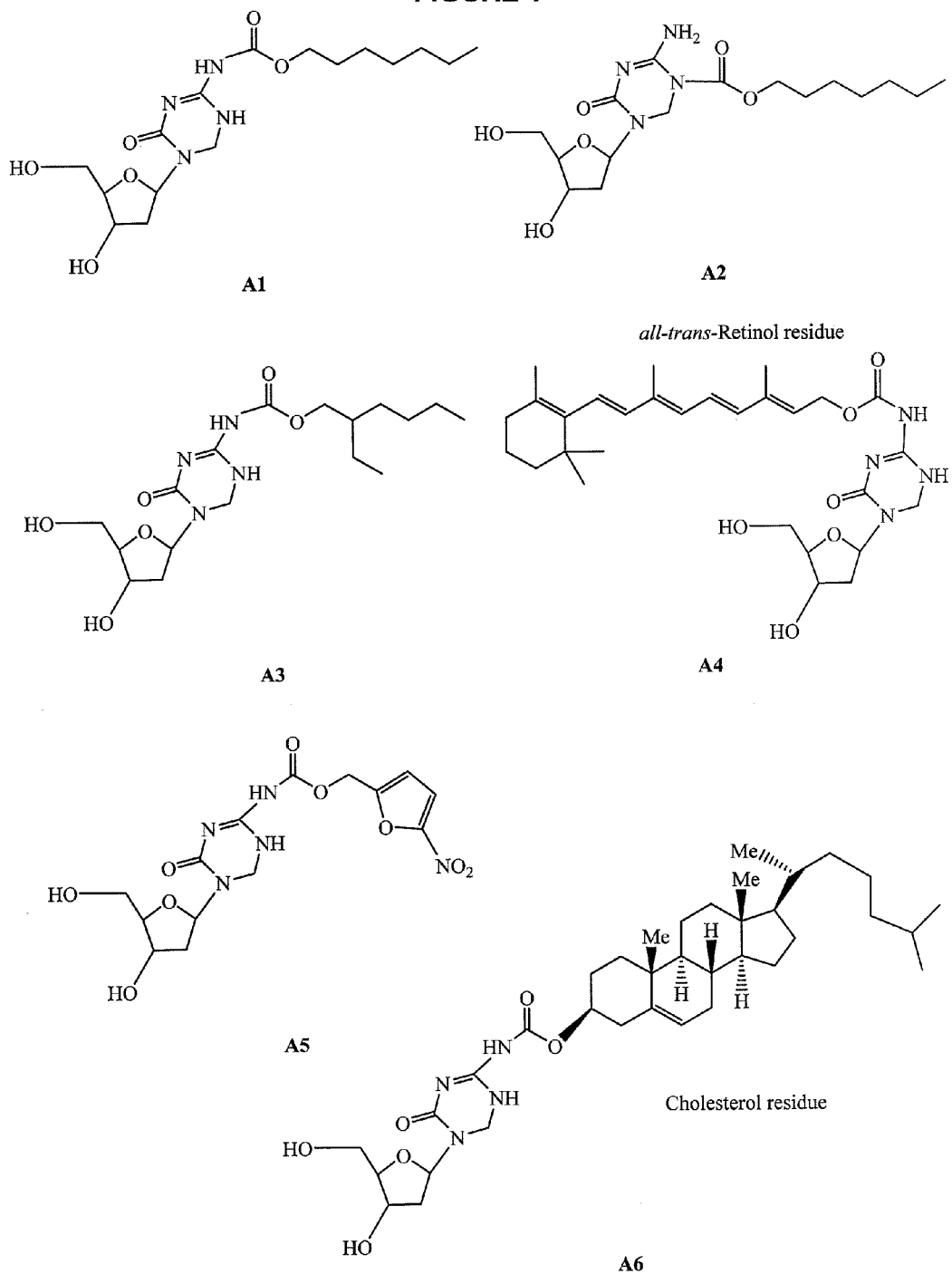
FIG. 1 displays structures of representative compounds of the invention.

The invention is directed to compounds which inhibit viral replication and the growth of cancerous cells. These compounds are hydrophobic prodrugs of bases, nucleosides, and nucleotides. The compounds are easily synthesized and comprise a parent compound, a hydrophobic group, and a linker which covalently attaches the parent compound to the hydrophobic group. Addition of the hydrophobic group and linker significantly improves the compound's pharmacokinetic properties over the unmodified parent compound.

The compounds of the invention are useful for inhibiting viral replication in cell culture as well as in antiviral therapy for animals and humans. In one embodiment, the compounds and methods of the invention are advantageous when used to target RNA viruses (viruses with a RNA genome), and retroviruses or other viruses otherwise replicated by a RNA intermediate. In another embodiment, the compounds and methods of the invention are advantageous for targeting DNA viruses (viruses with a DNA genome) such as hepatitis B virus, herpesviruses, and papilloma viruses. In one embodiment, the compounds are incorporated into both viral encoded and cellular encoded viral genomic polynucleotide sequences, thereby causing miscoding in progeny copies of the genomic virus, e.g., by tautomerism, which allows base mispairing (See, e.g., Moriyama et al., *Nucleic Acids Symp. Ser.* 42:131-132 (1999); Robinson et al., *Biochemistry* 37:10897-10905 (1998); Anensen et al., *Mutat. Res.* 476:99-107 (2001); Lutz et al., *Bioorg. Med. Chem. Lett.* 8:499-504 (1998); and Klungland et al., *Toxicology Lett.* 119:71-78 (2001)).

The compounds of the invention are useful for inhibiting the growth of cancer cells in cell culture as well as in treating cancer in animals and humans. In an exemplary embodiment, the cancer is a hematopoietic cancer, such as leukemia or lymphoma. In some embodiments, the prodrugs are efficiently incorporated into the bloodstream of the animal or human and, subsequently, into the polynucleotide sequence (either DNA or RNA) of a cancerous cell. The compounds of the invention have altered base-pairing properties which allow incorporation of mutations into the genome of the cancer cell, dramatically reducing the ability of the cancer cell to efficiently replicate its genome. In another embodiment, mutations are incorporated into transcription products, such as mRNA molecules or tRNA molecules, dramatically reducing the ability of the cancer cell to encode active proteins. As a result of these mutations, the cancer cells will either die, have diminished growth rates, or be unable to proliferate or metastasize.

II. Definitions

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent. —$S(O)_2HN$—, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl."

The term "alkylene", by itself or as part of another substituent, means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

"Acyl" refers to a moiety that is a residue of a carboxylic acid from which an oxygen atom is removed, i.e., —C(O)R, in which R is substituted or unsubstituted alkyl, substituted or unsubstituted heteroalkyl, substituted or unsubstituted heterocycloalkyl, substituted or unsubstituted aryl or substituted or unsubstituted heteroaryl.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, S and Si, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, typically aromatic, hydrocarbon substituent, which can be a single ring or multiple rings (up to three rings), which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')═NR"", —NR—C(NR'R")═NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R"" each preferably independently refer to hydrogen, substituted or unsubstituted alkyl, substituted or unsubstituted heteroalkyl, substituted or unsubstituted aryl, e.g., aryl substituted with 1-3 halogens, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', ═O, ═NR', ═N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")═NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system. R', R", R''' and R"" each preferably independently refer to hydrogen, substituted or unsubstituted alkyl, substituted or unsubstituted heteroalkyl, substituted or unsubstituted aryl, e.g., aryl substituted with 1-3 halogens, alkoxy or thioalkoxy groups, or arylalkyl groups. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S) and silicon (Si).

"Moiety" refers to the radical of a molecule that is attached to another structure.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups alos include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

The symbol ∿∿ ,whether utilized as a bond or displayed perpendicular to a bond indicates the point at which the displayed moiety is attached to the remainder of the molecule, solid support, etc.

The term "compounds of the invention" encompass hydrophobic prodrugs, as well as the unmodified parent compounds of the hydrophobic prodrugs.

The term "prodrug" comprises derivatives of active drugs which have been modified by the addition of a chemical group. This chemical group usually reduces or eliminates the drug's biological activity while, at the same time, conferring some other property to the drug. Once the chemical group has been cleaved from the prodrug, by hydrolysis, reduction, oxidation, light, heat, cavitation, pressure, and/or enzymes in the surrounding environment, the active drug is generated. Prodrugs may be designed as reversible drug derivatives and utilized as modifiers to enhance drug transport to site-specific tissues. Prodrugs are described in the art, for example, in R. L. Juliano (ed.), BIOLOGICAL APPROACHES TO THE CONTROLLED DELIVERY OF DRUGS, Annals of the New York Academy of Sciences, Vol 507 (1998); Hans Bundgaard (ed.), DESIGN OF PRODRUGS, Elsevier Science, (1986); and Kenneth Sloan (ed.), PRODRUGS: TOPICAL AND OCULAR DRUG DELIVERY, Drugs and the Pharmaceutical Sciences, Vol 53 (1992).

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", *Journal of Pharmaceutical Science* 66:1-19 (1997)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention can exist in tautomeric forms. In general, all tautomeric forms are equivalent and are encompassed within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In an exemplary embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23:128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "viral disease" refers to a condition caused by a virus. A viral disease is caused by a DNA virus, a RNA virus, or a retrovirus.

The term "vitamin K" refers to 2-methyl-1,4-naphthoquinone and derivatives thereof that have coagulation activity. The natural forms are substituted in position 3 of the quinone with an alkyl side chain. Examples of vitamin K include Vitamin $K_1$ (phylloquinones), and vitamin $K_2$ (menaquinones).

As used herein, the term "base" encompasses aryl and heteroaryl structures which are capable of covalent attachment to a sugar moiety. Examples include naturally-occurring bases such as adenine, guanine, cytosine, thymine and uracil. "Bases" also include non-natural bases, such as nitroindole, 5-aza-cytosine, and dihydro-5-aza-cytosine.

As used herein, the term "nucleoside" includes both the naturally occurring nucleosides (adenosine, guanosine, cytidine, thymidine, and uridine) and modifications thereof. Modifications include, but are not limited to, those providing chemical groups that incorporate additional charge, polarizability, hydrogen bonding, and electrostatic interaction to the nucleosides. Such modifications include, but are not limited to, peptide nucleic acids (PNAs), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, isobases, such as isocytidine and isoguanidine and the like. "Nucleosides" can also include non-natural bases, such as, for example, nitroindole, 5-aza-cytidine, 5-aza-2'-deoxycytidine, and dihydro-5-aza-2'-deoxycytidine. Modifications can also include derivitization with a quencher, a fluorophore or another moiety. "Nucleotides" are phosphate esters of nucleosides. Many of the chemical reactions which are utilized for nucleosides can also be utilized for nucleotides.

As used herein, "nucleic acid" encompasses bases, nucleosides, and nucleotides, and modifications thereof. Examples of modifications are listed in the definition of "nucleosides" above.

A "polynucleotide sequence" is a deoxyribonucleotide or ribonucleotide polymer in either single- or double-stranded form. Unless otherwise limited, "polynucleotide sequence" encompasses analogs of natural nucleotides.

A "genomic polynucleotide sequence" is a nucleotide polymer which is homologous to naturally occurring polynucleotide sequences (RNA or DNA) which are packaged by a viral particle. Typically, the packaged polynucleotide sequence encodes some or all of the components necessary for viral replication. The genomic polynucleotide sequence optionally includes nucleotide analogs. Polynucleotide sequences are homologous when they are derived from a polynucleotide sequence with a common sequence (an "ancestral" polynucleotide sequence) by natural or artificial modification of the ancestral polynucleotide sequence. Retroviral genomic polynucleotide sequences optionally encode a RNA which is competent to be packaged by a retroviral particle. Such polynucleotide sequences can be constructed by recombinantly combining a packaging site with a polynucleotide sequence of choice.

A "virally infected cell" is a cell transduced with a viral polynucleotide sequence. The polynucleotide sequence is optionally incorporated into the cellular genome, or is optionally episomal.

The "mutation rate" of a virus or polynucleotide sequence refers to the number of changes which occur upon copying the polynucleotide sequence, e.g., by a polymerase. Typically, this is measured over time, i.e., the number of alterations which occur during rounds of copying or generations of virus.

A "polymerase" refers to an enzyme that produces a polynucleotide sequence (DNA or RNA) which is complementary to a pre-existing polynucleotide template (DNA or RNA). For example, a RNA polymerase may be a RNA polymerase (viral or cellular) or a replicase. The polymerase may be either naturally occurring, or artificially (e.g., recombinantly) produced.

A "cell culture" is a population of cells residing outside of an animal. These cells are optionally primary cells (isolated from a cell bank, animal, or blood bank), secondary cells (cultured from one of the above sources), or long-lived, artificially maintained, in vitro cultures.

A "progressive loss of viability" refers to a measurable reduction in the replicative or infective ability of a population of viruses over time or in response to treatment with a prodrug of the invention.

A "viral particle" is genetic material substantially encoded by a RNA virus or a virus with a RNA intermediate, such as BVDV, HCV, or HIV. The presence of non-viral or cellular components in the particle is a common result of the replication process of a virus, which typically includes budding from a cellular membrane.

An "HIV particle" is a retroviral particle substantially encoded by HIV. The presence of non-HIV viral or cellular components in the particle is a common result of the replication process of HIV which typically includes budding from a cellular membrane. In certain applications, retroviral particles are deliberately "pseudotyped" by co-expressing viral proteins from more than one virus (often HIV and vesicular stomatitis virus (VSV)) to expand the host range of the resulting retroviral particle. The presence or absence of non-HIV components in an HIV particle does not change the essential nature of the particle, i.e., the particle is still produced as a primary product of HIV replication.

As used herein, "cancer" includes solid tumors and hematological malignancies. The former includes cancers such as breast, colon, and ovarian cancers. The latter include hematopoietic malignancies including leukemias, lymphomas and myelomas. This invention provides new effective methods and compositions for treatment and/or prevention of various types of cancer.

The term "patient" or "subject" refers to any warm-blooded animal, such as a mouse, rat, dog, or human.

A "pharmaceutically acceptable" component is one that is suitable for use in a patient without undue adverse side effects (such as toxicity, irritation, and allergic response) commensurate with a reasonable benefit/risk ratio.

A "safe and effective amount", or a "therapeutically effective amount", refers to the quantity of a component that is sufficient to yield a desired therapeutic response without undue adverse side effects (such as toxicity, irritation, or allergic response). In some embodiments, the desired therapeutic response is enhancing mutagenesis of a virus, diminishing the ability of a virus to produce active proteins, inhibiting replication of a virus, eliminating or diminishing the ability of a virus to produce infectious particles, or killing the virus or a virally infected cell. In other embodiments, the therapeutic response is halting or delaying the growth of a cancer, or causing a cancer to shrink, or not to metastasize. The specific safe and effective amount or therapeutically effective amount will vary with such factors as the particular condition being treated, the physical condition of the patient, the type of patient being treated, the duration of the treatment, the nature of concurrent therapy (if any), the specific formulations employed, and the structure of the compounds or its derivatives.

As used herein, the term "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

III. The Compounds

The compounds of the invention are hydrophobic prodrugs of bases, nucleosides, and nucleotides. These prodrugs comprise a parent compound, a hydrophobic group, and a linker which covalently attaches the parent compound to the hydrophobic group. Addition of the hydrophobic group and linker significantly improves the pharmacokinetic properties of the prodrug relative to the unmodified parent compounds.

The compounds of the invention are easily synthesized from commercially available starting materials and reagents. Synthetic schemes illustrating the preparation of the compounds are located in part B of this section. Detailed synthetic protocols and characterization data are supplied in Example 1.

A. Prodrug Components
i) Parent Compound

The prodrugs of the invention comprise a parent compound. In some embodiments, the parent compound is a base, nucleoside, or nucleotide. In other embodiments, the parent compound is a cytosine analog. In some embodiments, the cytosine analog is a derivative of 5-aza-cytosine, 5-aza-dC, and DHAdC. In other embodiments, the cytosine analog has a structure according to Formula I:

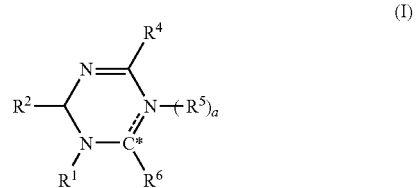

(I)

in which a is either 0 or 1. The dashed line represents a double bond between C* and N when a is 0. The symbol $R^2$ is a member selected from (=O) and $NR^7R^8$. $R^4$ is a member selected from H, halogen, $OR^3$, $NR^7R^8$, halogen, nitrile, and substituted and unsubstituted $(C_1-C_5)$alkyl. The symbol $R^6$ is a member selected from H, halogen, $OR^3$, $NR^3R^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl. $R^7$, $R^8$, $R^5$ and $R^1$ are members independently selected from H, $OR^3$, $NR^3R^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl. The symbol $R^3$ is independently selected from H, substituted or unsubstituted alkyl and substituted or unsubstituted acyl. The groups $R^7$ and $R^8$, $R^8$ and $R^5$, and $R^5$ and $R^6$, together with the atoms to which they are joined, optionally form a substituted or unsubstituted 5- to 7-membered ring. In the compounds of the invention, at least one member selected from $R^3$, $R^5$, $R^7$, and $R^8$, alone or together with the atom to which it is covalently bonded, is selected from carbamate and urea linkers.

In an exemplary embodiment, $R^1$ comprises a hydroxyl moiety. In another exemplary embodiment, $R^1$ comprises a saccharyl moiety. In yet another exemplary embodiment, $R^1$ is a structure according to Formula II:

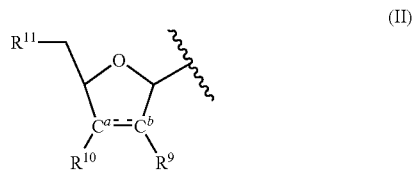

(II)

in which the dashed line represents a double bond between $C^a$ and $C_b$. $R^9$, $R^{10}$ and $R^{11}$ are members independently selected from H, —OH, —$OR^{12}$, —$NH_2$, —$NO_2$, —$SO_2NH_2$, $N_3$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl. The symbol $R^{12}$ is selected from an amino acid and a peptide comprising between 2 and 5 amino acids. The symbols $R^9$ and $R^{10}$, and $R^{10}$ and $R^{11}$, together with the atoms to which they are joined, optionally form a substituted or unsubstituted 5- to 7-membered ring.

In another exemplary embodiment, the symbols $R^9$, $R^{10}$ and $R^{11}$ are members independently selected from H, OH, $(R^{13})_3SiO—$, and a structure according to Formula III:

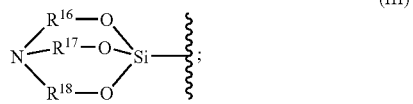
(III)

in which each $R^{13}$ is independently selected from substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl. More than one $R^3$, together with the atoms to which they are joined, optionally form a substituted or unsubstituted 5- to 7-membered ring. The symbols $R^{16}$, $R^{17}$, and $R^{18}$ are independently selected from substituted and unsubstituted alkyl. In another exemplary embodiment, the symbols $R^{16}$, $R^{17}$, and $R^{18}$ are ethyl.

ii) Hydrophobic Group

The prodrugs of the invention also comprise a hydrophobic group. This group should improve the prodrug's absorption in the body and distribution to organs by increasing its lipophilicity. $C_6$-$C_{10}$ alkyl groups, lipophilic vitamins, and cholesterol are three exemplary hydrophobic groups.

In some embodiments, the hydrophobic group is $R^{14}$ from Formula IV. $R^{14}$ is selected from substituted or unsubstituted alkyl, substituted or unsubstituted heteroalkyl, substituted or unsubstituted cycloalkyl, substituted or unsubstituted heterocycloalkyl, substituted or unsubstituted acyl, substituted or unsubstituted aryl, and substituted or unsubstituted heteroaryl, an amino acid, and a peptide comprising between 2 and 5 amino acids. In another exemplary embodiment, $R^{14}$ is selected from substituted or unsubstituted $(C_4$-$C_{12})$alkyl, benzyl, 2-nitro-furanyl, retinol, α-tocopherol, calciferol, vitamin K, cholesterol,

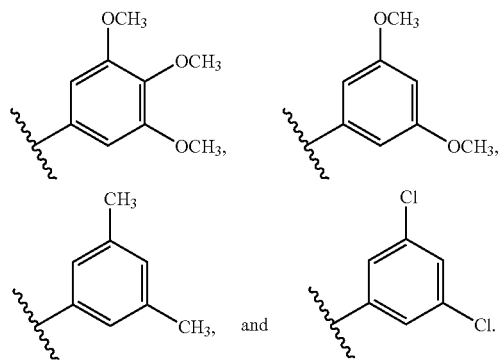

In yet another exemplary embodiment, $R^{14}$ is substituted or unsubstituted $(C_6$-$C_{10})$alkyl. In still another exemplary embodiment, $R^{14}$ is unsubstituted $(C_6$-$C_{10})$alkyl.

In other embodiments, the chemical group is $R^{15}$ from Formula V. $R^{15}$ is selected from substituted or unsubstituted alkyl, substituted or unsubstituted heteroalkyl, substituted or unsubstituted cycloalkyl, substituted or unsubstituted heterocycloalkyl, substituted or unsubstituted acyl, substituted or unsubstituted aryl, and substituted or unsubstituted heteroaryl, an amino acid, and a peptide comprising between 2 and 5 amino acids. In another exemplary embodiment, $R^{15}$ is selected from substituted or unsubstituted $(C_4$-$C_{12})$alkyl, benzyl, 2-nitro-furanyl, retinol, α-tocopherol, calciferol, vitamin K, cholesterol,

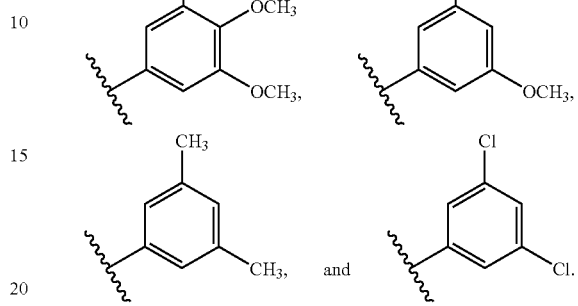

In yet another exemplary embodiment, $R^{15}$ is substituted or unsubstituted $(C_6$-$C_{10})$alkyl. In still another exemplary embodiment, $R^{15}$ is unsubstituted $(C_6$-$C_{10})$alkyl.

iii) Linker

The prodrug also contains a linker which covalently attaches the hydrophobic group to the parent compound. This linker should be stable under certain conditions, and yet labile in others. For example, orally available compounds preferably include a linker that is stable under acidic conditions and yet labile under the enzymatic conditions that exist in the liver. Carbamate groups and urea groups are two exemplary linkers.

In an exemplary embodiment, a structure according to Formula I contains a carbamate or urea linker. In yet another exemplary embodiment, a structure according to Formula I has at least one member selected from $R^3$, $R^5$, $R^7$, and $R^8$, which, either alone or together with the nitrogen atom to which it is covalently bonded, is either a carbamate or a urea.

In an exemplary embodiment, $R^3$, $R^5$, $R^7$, and $R^8$ are independently selected from H and a structure according to Formula IV or V:

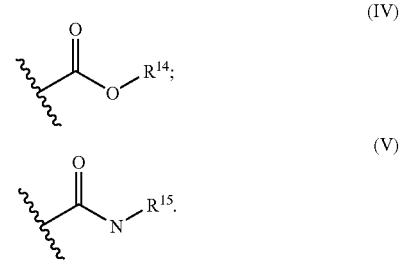

If $R^8$ is a structure according to either Formula IV or Formula V, then $R^7$ is H.

iv) Pharmacokinetic Properties

The covalent attachment of a hydrophobic group and linker to a parent compound significantly improves its pharmacokinetics relative to its unmodified form. Pharmacokinetics are improved either through an increase or a decrease in certain pharmacokinetic properties.

In some embodiments, prodrug pharmacokinetics are improved, relative to those of the parent compound, through an increase in a pharmacokinetic property selected from half-life ($t_{1/2}$), oral bioavailability, lipophilicity, stability in acidic pH or uptake from the gastrointestinal tract. In some embodiments, the pharmacokinetic property is increased by an amount between 10% and 600%. In some embodiments, the pharmacokinetic property is increased by an amount between 10% and 100%. In some embodiments, the pharmacokinetic property is increased by an amount between 400% and 500%. In some embodiments, the half-life is increased by an amount between 200% and 500%. In some embodiments, the oral bioavailability is increased by an amount between 200% and 400%.

In other embodiments, prodrug pharmacokinetics are improved, relative to its unmodified form, through a decrease in a pharmacokinetic property such as a reduction in the first-pass effect. In some embodiments, the first-pass effect is reduced by an amount between 10% and 100%. In other embodiments, the first-pass effect is reduced by an amount between 400% and 500%.

The improved pharmacokinetic property is observed in a patient selected from a mouse, rat, dog, or human.

Pharmacokinetic data for the compounds of the invention have been acquired in rat and dog models. The laboratory protocol for the rat study is provided in Example 2, while the laboratory protocol for the dog study is provided in Example 4. In both studies, DHAdC was the parent compound, the hydrophobic group was a $C_7$-$C_9$ unsubstituted alkyl chain, and the linker was a carbamate moiety. Oral administrations of the DHAdC prodrugs were tested against IV and oral administrations of the parent compound. The results of the rat study are provided in Example 3, while the results of the dog study are provided in Example 5.

In the rat study, both prodrugs had half lives which were between 300-400% longer than DHAdC. In addition, the prodrugs reached the circulatory system (as evidenced by Oral Bioavailability) in amounts between 200-300% greater than DHAdC. Because the prodrug versions of DHAdC are more effective at reaching the target cells than DHAdC alone, these compounds are more effective viral and cancer inhibitors.

The laboratory protocol for the lipophilicity study is provided in Example 6, while the lipophilicity data for the compounds of the invention are described in Example 7.

B. Prodrug Preparation

The following exemplary schemes 1-7 illustrate methods of preparing the compounds of the invention. These methods are not limited to producing the compounds listed, but can be used to prepare other compounds as well. The compounds of the invention can also be produced by methods not explicitly illustrated in the schemes. The compounds can be prepared using readily available starting materials or known intermediates.

The carbonyl of compound 1 can be protected according to the method of Scheme 1.

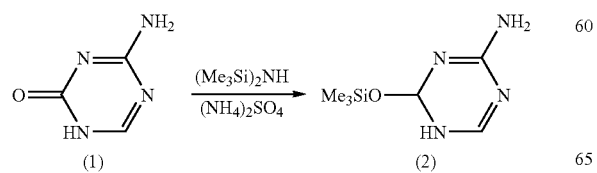

In this scheme, a trimethylsilyl protecting group is added to the carbonyl of commercially available 5-azacytosine (CAS #: 931-86-2, Sigma Chemical Company).

Compound 2 can be attached to a protected saccharide according to the method of Scheme 2.

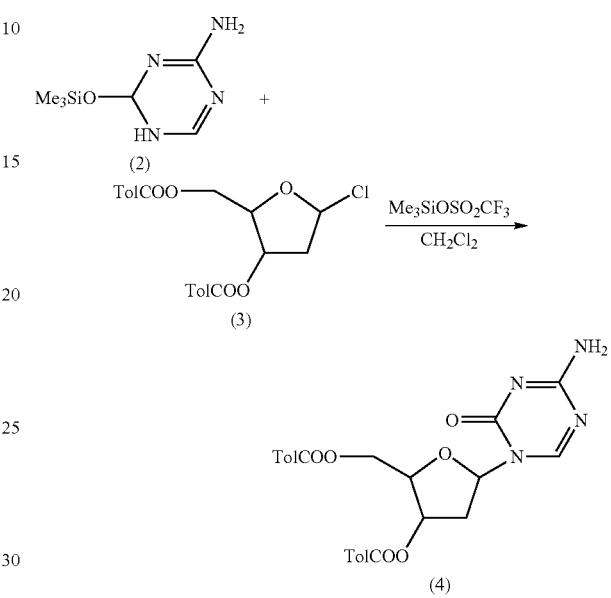

In Scheme 2, compound 2 is reacted with compound 3 in dichloromethane to produce compound 4. Compound 4 represents a mixture of approximately 70% β-anomer 4a and 30% α-anomer 4b.

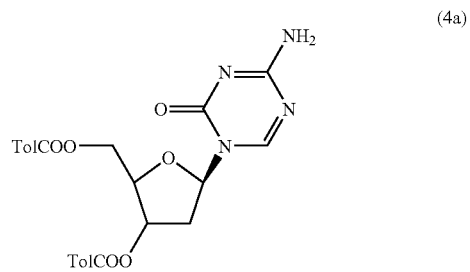

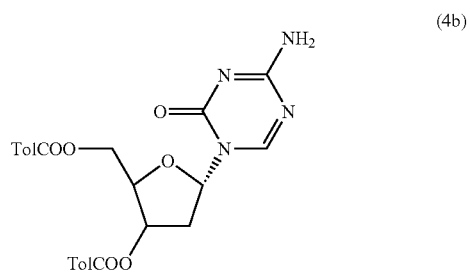

The double bond at the 5-position in compound 4 can be reduced with sodium borohydride according to the method of Scheme 3.

Scheme 3

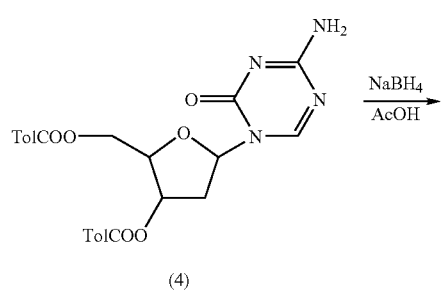

(4)

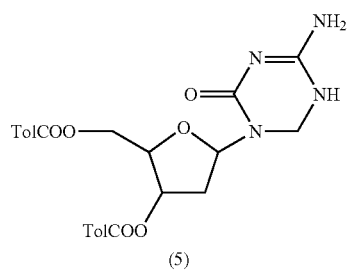

(5)

In Scheme 3, compound 4 is reacted with sodium borohydride in acetic acid to produce compound 5. Compound 5 represents a mixture of approximately 70% β-anomer 5a and 30% α-anomer 5b.

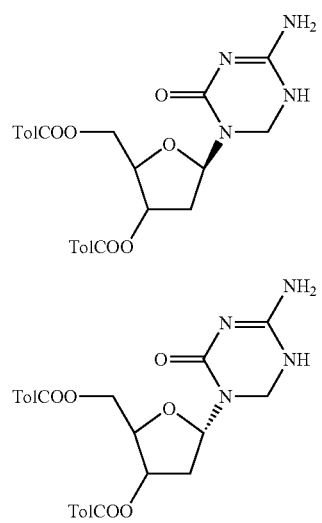

(5a)

(5b)

The pure β-anomer 5a is separated from the α-anomer 5b through recrystallization in methanol. The protecting groups are removed from compound 5a through the method according to Scheme 4.

Scheme 4

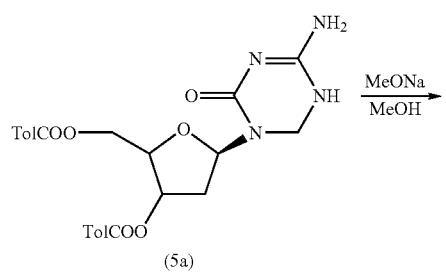

(5a)

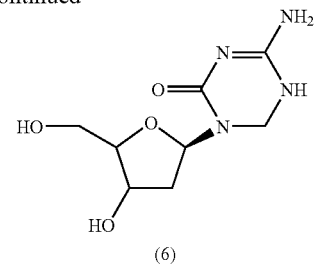

(6)

Adding sodium methoxide to compound 5a in methanol produces the deprotected compound 6.

A mixture of exo and endo N-acylated products can be produced according to the method of Scheme 5.

Scheme 5

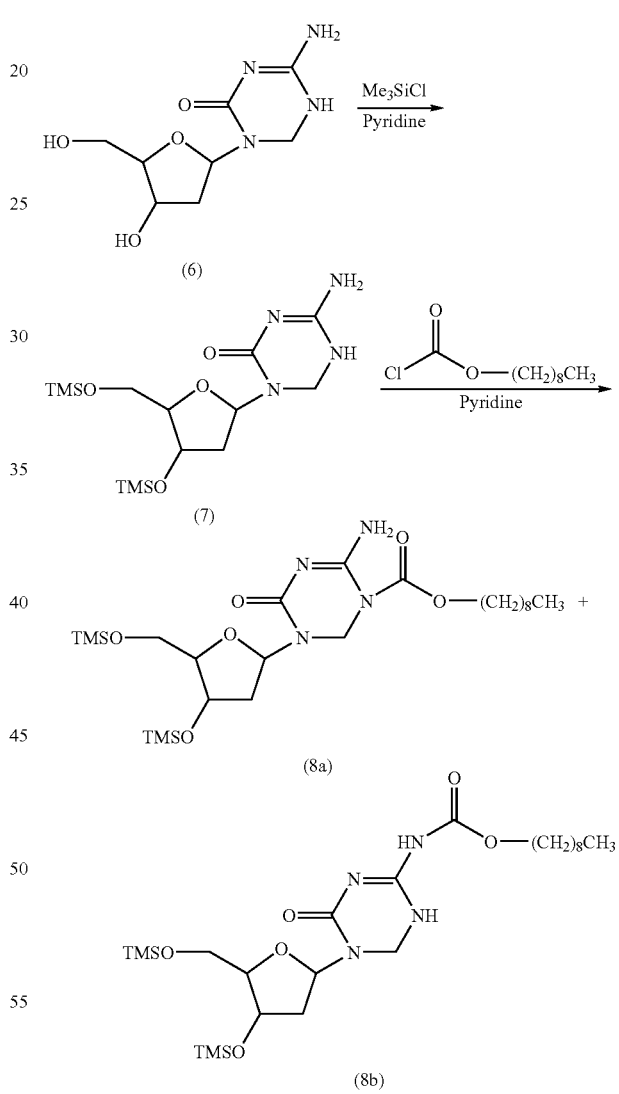

In Scheme 5, the hydroxyl groups of compound 6 are first protected using TMS chloride to form compound 7. Subsequently, the treatment of 7 with one equivalent of the appropriate chloroformate produces a mixture of endo-N-acylated product 8a and exo-N-acylated product 8b. The main endo-N-acylated product 8a is separated from the exo-N-acylated isomer 8b by flash chromatography on silica gel.

The pure exo-N-acylated isomer can be obtained by the method of Scheme 6.

Scheme 6

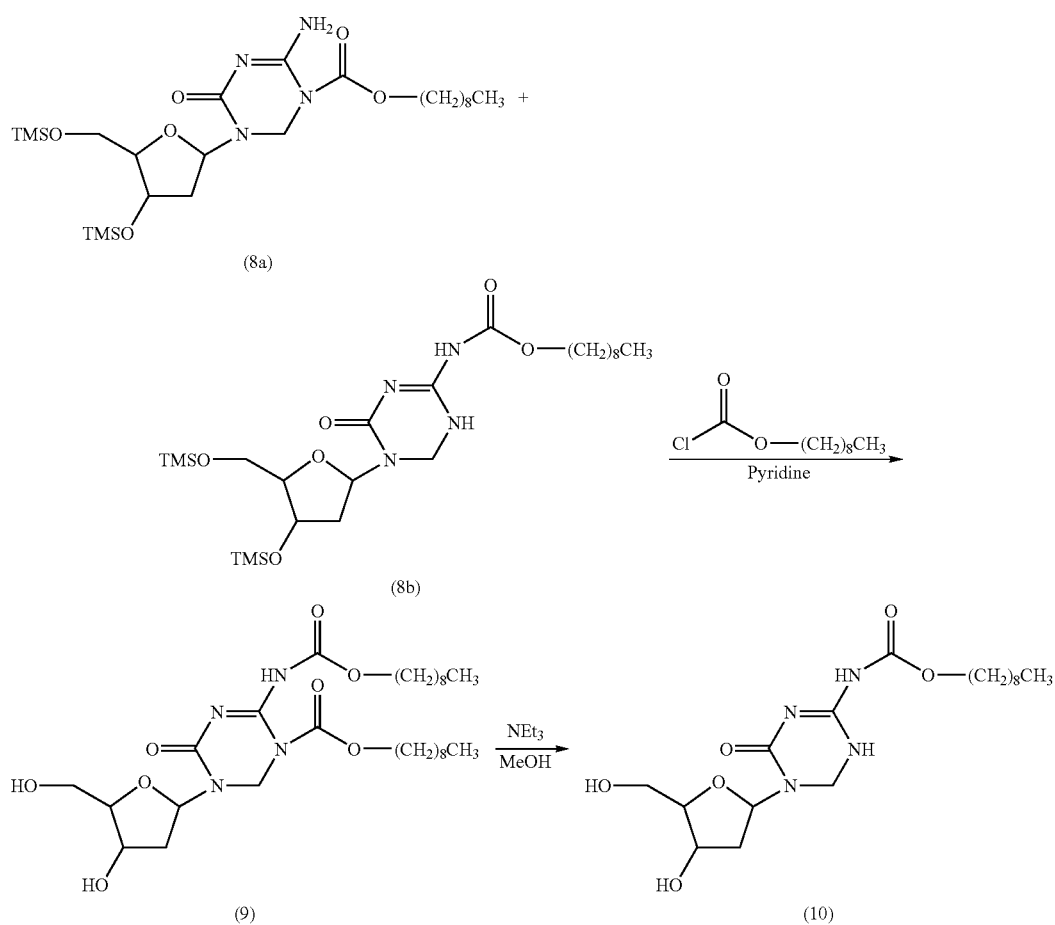

In Scheme 6, compounds 8a and 8b are first treated with an excess of a chloroformate to create the bis-N-acylated compound 9. Subsequent deprotection of the endo-N-acylated moiety from compound 9 with triethylamine in methanol produces the exo-N-acylated isomer 10 in a high overall yield.

The endo-N-acylated isomer 14 can be obtained from benzyloxycarbonyl-protected DHAdC 11 by the method of Scheme 7.

Scheme 7

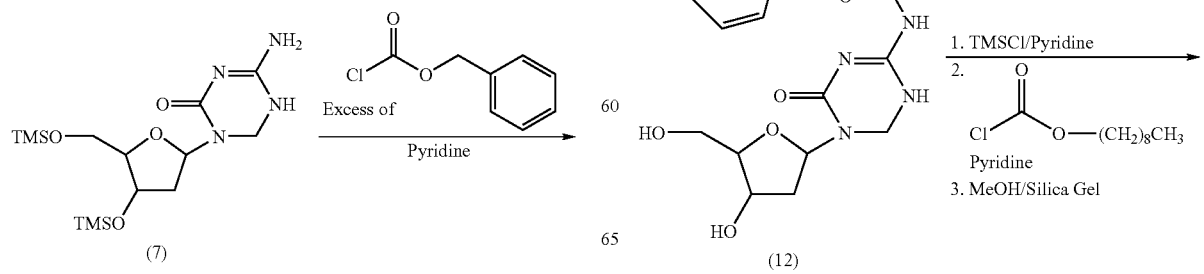

-continued

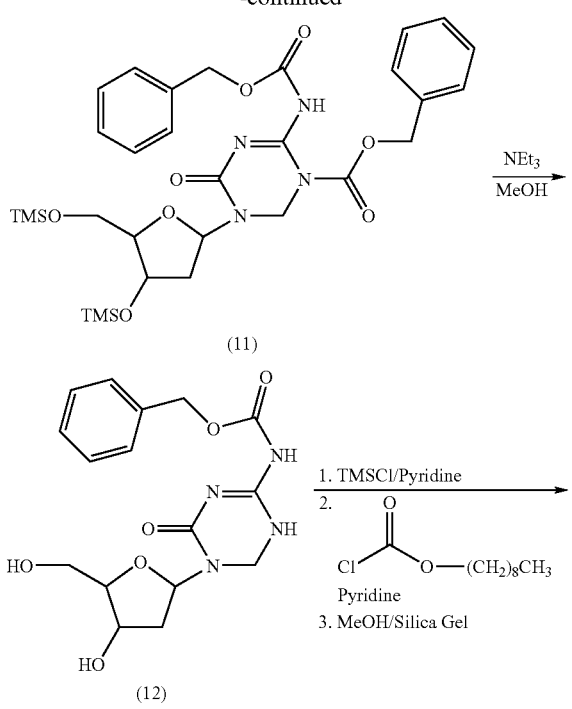

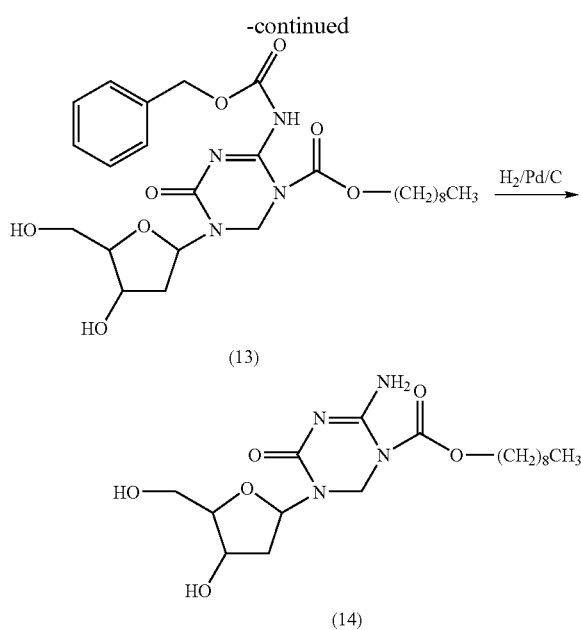

In Scheme 7, compound 7 is first treated with an excess of benzyloxychloroformate to create the bis-N-acylated compound 11. Subsequent deprotection of the endo-N-acylated moiety from compound 11 with triethylamine in methanol produces the exo-N-acylated isomer 12. Treatment with an amount of chloroformate will create compound 13. Catalytic hydrogenation of compound 13 produces the endo-N-acylated isomer 14.

IV. The Viruses

The compounds of the invention possess activity against viruses. Some of these viruses are able to integrate their viral genome into the genome of a cell. Examples of viruses which have this ability include, but are not limited to, retroviruses. In an exemplary embodiment, the virus is HIV and its variants, such as HIV-1, HIV-2, HTLV-1, HTLV-II, and SIV. In another embodiment, the virus is a DNA virus such as hepatitis B virus, herpesviruses (e.g., Herpes Simplex Virus, CytoMegaloVirus (CMV), Epstein-Barr Virus, (EBV)), smallpox virus, or human papilloma virus (e.g., HPV). Alternatively, the viral genome can be episomal. These include many human and animal pathogens: flaviviruses, such as dengue fever, West Nile, and yellow fever; pestiviruses, such as bovine viral diarrhea (BVD), and hepaciviruses, such as hepatitis C; filoviruses such as ebola; parainfluenza viruses, including respiratory syncytial; rubulaviruses, such as mumps; morbillivirus, such as measles; picornaviruses, including the echoviruses; the coxsackieviruses; the polioviruses; the togaviruses, including encephalitis; coronaviruses, including Severe Acute Respiratory Syndrome (SARS); rubella; bunyaviruses; reoviruses, including rotaviruses; rhabdoviruses; arenaviruses, such as lymphocytic choriomeningitis, as well as other RNA viruses of man and animal.

Retroviruses that can be targeted include HTLV viruses such as HTLV-1 and HTLV-2, adult T-cell leukemia (ATL), HIV-1 and HIV-2 and SIV. In some embodiments, the HIV virus is resistant to non-nucleoside reverse transcriptase inhibitors. In certain embodiments, the virus is hepatitis A or hepatitis B. See, Knipe et al. FIELDS VIROLOGY, 4th ed. Lippincott, Williams, and Wilkins (2001). Further information regarding viral diseases and their replication can be found in White and Fenner, MEDICAL VIROLOGY, 4th ed. Academic Press (1994) and in Zuckerman, Banatvala and Pattison (ed.), PRINCIPLES AND PRACTICE OF CLINICAL VIROLOGY, John Wiley and Sons (1994).

V. Methods of Treating Viral Diseases

The compounds, methods, and pharmaceutical compositions of the present invention are useful in the treatment of viral diseases. In one aspect, the invention provides a method of treating a viral disease comprising administering to a subject in need of such treatment a therapeutically effective amount of a compound according to Formula I. In an exemplary embodiment, the viral disease is caused by a virus that is a member selected from a RNA virus and a DNA virus. In another exemplary embodiment, the virus is selected from a retrovirus and a ribovirus. In yet another exemplary embodiment, the retrovirus is selected from HIV and Hepatitis B. In still another exemplary embodiment, the ribovirus is Hepatitis C.

In one embodiment for the treatment of viral diseases, the compounds of the invention are efficiently delivered into the bloodstream of a patient, such as a mouse, rat, dog or human, and subsequently incorporated into the genome of the virus of interest. The compounds of the invention either have phosphodiester linkages or acquire phosphodiester linkages, enabling them to be incorporated into the viral genome by a polymerase. In some embodiments, the compounds of the invention have altered base-pairing properties which allow the incorporation of mutations into the viral genome, thereby increasing the total number of mutations. Increases in the total number of mutations result in reduced viral population growth rates, as well as decreased viability of progeny virus.

Methods of Treating HIV

The compounds of the invention are useful for treating HIV infections and other retroviral infections. The compounds of the present invention are particularly well-suited to treat HIV strains that are resistant to chain-terminating nucleosides. In one embodiment, compounds of the invention are used for treating an HIV strain which is resistant to a chain-terminating nucleoside.

HIV strains resistant to chain-terminating nucleosides are known and mutations in the reverse transcriptase (RT) enzyme responsible for the resistance have been analyzed. Two mechanisms of viral resistance toward chain-terminating nucleosides have been described. In the first mechanism, the virus discriminates between a chain-terminating nucleoside and a naturally occurring nucleoside, thus preventing the chain-terminating nucleoside's incorporation into the viral genome. For example, chain-terminating nucleoside-resistant viral strains contain a version of HIV-RT which recognizes the absence of a 3'-OH group, a feature present in some chain-terminating nucleosides (see, e.g., Sluis-Cremer et al., Cell. Mo. Life Sci. 57:1408-1422 (2000)). In the second mechanism, the virus excises the chain-terminating nucleoside after its incorporation into the viral genome via pyrophosphorolysis in the presence of nucleotides (see, e.g., Isel et al., J. Biol. Chem. 276:48725-48732 (2001)). In pyrophosphorolysis, also known as reverse nucleotide polymerization, pyrophosphate acts as an acceptor molecule for the removal of the chain-terminating nucleoside. Removal of the chain-terminating nucleoside frees RT to incorporate the natural nucleotide substrate and maintain accurate viral replication. ATP has also been proposed as an acceptor molecule for the removal of chain-terminating nucleosides and is referred to as primer unblocking (see, e.g., Naeger et al., Nucleosides Nucleotides Nucleic Acids 20:635-639 (2001)).

The compounds of the invention can reduce viral resistance through the first mechanism mentioned above. Because the compounds of the invention comprise sugars with hydroxyls at the 3' position, it is believed that HIV-RT should be unable to differentiate between them and natural nucleosides.

In general, the compounds of the invention will reduce viral resistance compared to treatment with chain-terminating nucleosides. Currently approved chain-terminating nucleosides target one aspect of the viral growth cycle, replication, and immediately attempt to stop it through chain termination. Since the antiviral's effect is narrowly targeted and abrupt, there is great selective pressure for the development of resistant viral strains. The compounds of the invention act by a different method. The compounds act through the gradual accumulation of random mutations in the viral genome. This corresponds to the gradual inactivation of potentially any of the viral proteins. Since the effect of the compounds of the invention is broadly targeted and gradual, there is less selective pressure for the emergence of resistant viral strains.

Cross resistance between chain-terminating nucleosides and the compounds of the invention can be tested by determining the $EC_{50}$ for a prodrug in a wild-type HIV strain and in a HIV strain resistant to one or more chain-terminating nucleosides. If the $EC_{50}$ for the prodrug is higher in the chain-terminating nucleoside resistant strain than in the wild-type strain, then cross resistance has occurred. Experiments have demonstrated that cross resistance is unlikely to develop between chain-terminating nucleosides and compounds of the invention.

VI. Cancer

The compounds of the invention possess activity against cancer. In some embodiments, the prodrugs possess activity against hematological malignancies. Hematological malignancies, such as leukemias and lymphomas, are conditions characterized by abnormal growth and maturation of hematopoietic cells.

Leukemias are generally neoplastic disorders of hematopoietic stem cells, and include adult and pediatric acute myeloid leukemias (AML), chronic myeloid leukemia (CML), acute lymphocytic leukemia (ALL), chronic lymphocytic leukemia (CLL), hairy cell leukemia and secondary leukemia. Myeloid leukemias are characterized by infiltration of the blood, bone marrow, and other tissues by neoplastic cells of the hematopoietic system. CLL is characterized by the accumulation of mature-appearing lymphocytes in the peripheral blood and the infiltration of these mature-appearing lymphocytes into the bone marrow, spleen and lymph nodes.

Specific leukemias include acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas are generally neoplastic transformations of cells that reside primarily in lymphoid tissue. Among lymphomas, there are two major distinct groups: non-Hodgkin's lymphoma (NHL) and Hodgkin's disease. Lymphomas are tumors of the immune system and generally involve both T- and B-cells. Lymphomas are typically found in bone marrow, lymph nodes, the spleen and the circulatory system. Treatment protocols include removal of bone marrow from the patient, purging the bone marrow of tumor cells (often using antibodies directed against antigens present on the tumor cell type), followed by storage of the bone marrow. After the patient receives a toxic dose of radiation or chemotherapy, the purged bone marrow is reinfused in order to repopulate the patient's hematopoietic system.

Other hematological malignancies include myelodysplastic syndromes (MDS), myeloproliferative syndromes (MPS) and myelomas, such as multiple myeloma and solitary myeloma. Multiple myeloma (also called plasma cell myeloma) affects the skeletal system and is characterized by multiple tumorous masses of neoplastic plasma cells scattered throughout the system. It may also spread to lymph nodes and other sites such as the skin. Solitary myeloma involves solitary lesions that tend to occur in the same locations as multiple myeloma.

The compounds of the invention are also directed against other cancers. Such cancers include those characterized by solid tumors. Examples of other cancers of concern are skin cancers, including melanomas, basal cell carcinomas, and squamous cell carcinomas. Epithelial carcinomas of the head and neck are also encompassed by the present invention. These cancers typically arise from mucosal surfaces of the head and neck and include salivary gland tumors.

The present invention also encompasses cancers of the lung. Lung cancers include squamous or epidermoid carcinoma, small cell carcinoma, adenocarcinoma, and large cell carcinoma. Breast cancer is also included.

The present invention also encompasses gastrointestinal tract cancers. Gastrointestinal tract cancers include esophageal cancers, gastric adenocarcinoma, primary gastric lymphoma, colorectal cancer, small bowel tumors and cancers of the anus. Pancreatic cancer and cancers that affect the liver are also of concern, including hepatocellular cancer. The present invention also includes treatment of bladder cancer and renal cell carcinoma.

The present invention also encompasses prostatic carcinoma and testicular cancer.

Gynecologic malignancies are also encompassed by the present invention and include ovarian cancer, carcinoma of the fallopian tube, uterine cancer, and cervical cancer.

Treatment of sarcomas of the bone and soft tissue are encompassed by the present invention. Bone sarcomas include osteosarcoma, chondrosarcoma, and Ewing's sarcoma.

The present invention also encompasses malignant tumors of the thyroid, including papillary, follicular, and anaplastic carcinomas.

VII. Methods of Treating Cancer

The compounds, methods, and pharmaceutical compositions of the invention are useful in the treatment of cancer. In one aspect, the invention provides a method of treating cancer comprising administering to a subject in need of such treatment a therapeutically effective amount of a compound according to Formula I. In an exemplary embodiment, the cancer is a leukemia, lymphoma, or other hematopoietic cancer.

In one embodiment for the treatment of cancer, the compounds of the invention are efficiently delivered into the bloodstream of a patient, such as a mouse, rat, dog or human, and subsequently incorporated into a polynucleotide sequence (either DNA or RNA) of a cancerous cell. In some embodiments, the compounds of the invention have phosphodiester linkages or can acquire phosphodiester linkages, allowing them to be incorporated into the genome of a cancer cell by a polymerase. In another embodiment, the compounds of the invention have altered base-pairing properties and are incorporated into the cancer cell genome. Incorporation subsequently increases the number of mutations in the cancer cell. In another embodiment, mutations are incorporated into transcription products, e.g., mRNA molecules that encode proteins or tRNA molecules useful for protein translation. The mutated transcription products possess altered amino acid sequences which often result in inactive proteins. Regardless of the method of introduction, an increase in the number of mutations in the cancer cell causes reduced population growth rates, decreased viability of progeny cells, diminished ability to proliferate or metastasize, and cancer cell death.

Those of skill in the art are aware of methods to test the effectiveness of compounds in treating cancer. For example, cancer cells of interest can be grown in culture and incubated in the presence of varying concentrations of the compounds of the present invention. Frequently, the uptake of viral dyes, such as MTT, is used to determine cell viability and cell proliferation. When inhibition of cell proliferation is seen, the $IC_{50}$ of the compound can be determined. Those of skill in the art will also know to test the compounds of the present invention in animal models. For example, the compounds of the invention are injected into nude mice with transformed cancer cells. The data gathered in tissue culture models and animal models can be extrapolated by those of skill in the art for use in human patients.

VIII. Assays for Detecting Compounds of the Invention

A. Assays for Mutagenic Nucleic Acids

Nucleic acids are incorporated into the genome of a virus or a cell with an efficiency of at least about 0.1%. In some cases, the incorporation is at least about 5%, and most preferably equal to that of a naturally occurring complementary polynucleotide sequence when compared in equal amounts in an in vitro assay. Thus, an error rate of about 1 in 1000 bases or more would be sufficient to enhance mutagenesis of the virus. The ability of a nucleic acid to cause incorrect base pairing may be determined by testing and examining the frequency and nature of mutations produced by the incorporation of a compound of the invention into DNA or RNA. These mutation rates can vary widely. It has been reported, for example, that the mutation rates in lytic RNA viruses (such as influenza A) are about 300 times higher than in DNA viruses (Drake, *Proc. Natl. Acad. Sci. USA* 90:4171-4175 (1993)). Retroviruses, however, have mutation rates that are an order of magnitude lower, on average, than lytic RNA viruses.

Assays for the incorporation rates of altered nucleotides are analogous to those used for incorporation of deoxynucleoside triphosphates by DNA polymerases (Boosalis, et al., *J. Biol. Chem.* 262:14689-14698 (1987)). Those of skill in the art will recognize that such assays measure a compound's ability to inhibit a cellular polymerase or measure the replicative capability of a virus that has been treated with an altered nucleotide. In selected situations direct determination of the frequency of mutations that are introduced into the viral genome (Ji and Loeb, *Virol.*, 199:323-330 (1994)) can be made.

For example, in the case of HIV, the viral RNA or the incorporated HIV DNA is isolated and then copied using reverse transcriptase PCR (RT-PCR). The region of the genome copied corresponds to a 600 nucleotide segment in the reverse transcriptase gene. After 70 rounds of RT-PCR, the copied DNA or RNA is treated with restriction enzymes and ligated into a plasmid. After transfection of the plasmid into *E. coli*, individual clones are obtained and the amplified segment within the plasmid is sequenced. Mutations within this region are determined by computer aided analysis, comparing the individual sequences with control viral sequences obtained by parallel culturing of the same virus in the absence of the RNA analog. For each nucleotide, determinations are carried out after ten sequential rounds of viral passage or at the point of extinction for viral detection. Analogous procedures would be effective for other viruses of interest and would be readily apparent to those of skill in the art.

A comparison of incorporation of compounds of the invention among the polymerases of interest can be carried out using a modification of the "minus" sequencing gel assay for nucleotide incorporation. A $5'$-$^{32}$P-labeled primer is extended in a reaction containing three of the four nucleoside triphosphates and a compound of the invention in triphosphate form. The template can be either RNA or DNA, as appropriate. Elongation of the primer past the template nucleotide that is complementary to the nucleotide that is omitted from the reaction will depend upon, and be proportional to, the incorporation of the analog. The degree of analog incorporation is calculated as a function of the percent of oligonucleotide that is extended on the sequencing gel from one position to the next. Incorporation is determined by autoradiography followed by either densitometry or cutting out each of the bands and counting radioactivity by liquid scintillation spectroscopy. Those of skill in the art will recognize that similar experiments can be done to determine the incorporation of the compounds of the invention into polynucleotide sequences in cancer cells.

When a compound of the invention is administered to virally infected cells, either in vitro or in vivo, a population of cells is produced comprising a highly variable population of replicated homologous viral polynucleotide sequences. This population of highly variable cells results from administering mutagenic compounds of the invention to virally infected cells and increasing the mutation rate of the virus population. Thus, the highly variable population of viruses is an indicator that the mutation rate of the virus was increased by the administration of the compounds of the invention. Measuring the variability of the population provides an assessment of the viability of the viral population. In turn, the viability of the viral population is a prognostic indicator for the health of the cell population. For example, low viability for an HIV population in a human patient corresponds to an improved outlook for the patient.

In some embodiments, the mutagenic compound of the invention will be water soluble and have the ability to rapidly enter the target cells. Lipid soluble analogs are also encompassed by the present invention. If necessary, the compounds of the invention are phosphorylated by cellular kinases and incorporated into RNA or DNA.

B. Assays of Viral Replication

Those of skill in the art recognize that viral replication or infectivity correlates with the ability of a virus to cause disease. That is, a highly infectious virus is more likely to cause disease than a less infectious virus. In a preferred embodiment, a virus that has incorporated mutations into its genome as a result of treatment with the compounds of this invention will have diminished viral infectivity compared to untreated virus. Those of skill in the art are aware of methods to assay the infectivity of a virus. (See, e.g., Condit, *Principles of Virology*, in FIELDS VIROLOGY, 4th Ed. 19-51 (Knipe et al., eds., 2001)).

For example, a plaque forming assay can be used to measure the infectivity of a virus. Briefly, a sample of virus is added to an appropriate medium and serial dilutions are plated onto confluent monolayers of cells. The infected cells are overlaid with a semisolid medium so that each plaque develops from a single viral infection. After incubation, the plates are stained with an appropriate dye so that plaques can be visualized and counted.

Some viruses do not kill cells, but rather transform them. The transformation phenotype can be detected by, for example, formation of foci after loss of contact inhibition. The virus is serially diluted and plated onto monolayers of contact inhibited cells. Foci can be detected with an appropriate dye and counted to determine the infectivity of the virus.

Another method to determine virus infectivity is the endpoint method. The method is appropriate for viruses that do not form plaques or foci, but that do have a detectable pathology or cytopathic effect (CPE) in cultured cells, embryonated eggs, or animals. A number of phenotypes are measurable as CPEs, including rounding, shrinkage, increased refractility, fusion, syncytia formation, aggregation, loss of adherence or lysis. Serial dilutions of virus are applied to an appropriate assay system and after incubation, CPE is assayed. Statistical methods are available to determine the precise dilution of virus required for infection of 50% of the cells. (See, e.g., Spearman, *Br. J. Psychol.* 2:227-242 (1908); and Reed and Muench, *Am. J. Hyg.* 27:493-497 (1938)).

Measurements of viral replication can also be performed indirectly due to the difficulty in culturing viruses. For example, a replicon assay, which measures the inhibition of a self replicating genetic element, can be used to determine the extent of a virus's replication. HIV viral replication can be determined from measuring levels of p24 antigen. One exemplary means to determine antiviral activity is with CEM-SS cells and virus (e.g., HIV-$1_{RF}$) (MOI=0.01) using the XTT (2,3-bis[2-methoxy-4-nitro-5-sulfophenyl]-5-[(phenylamino)carbonyl]-2H-tetrazolium hydroxide) cytoprotection assay (see, e.g., Weislow, et al, *J. Natl. Canc. Inst.* 81:577-586 (1989); Rice *PNAS* 90:9721-9724 (1993); and Rice *Antimicrob. Agents Chemother.* 41:419-426 (1997)). Briefly, cells are infected with HIV-$1_{RF}$ (or other virus to be tested) in the presence of various dilutions of the compounds of the invention. The cultures are incubated for seven days. During this time control cultures without protective compounds (i.e., compounds with anti-viral activity) replicate virus, induce syncytia, and result in about 90% cell death. The cell death is measured by XTT dye reduction. XTT is a soluble tetrazolium dye that measures mitochondrial energy output, similar to MTT. Positive controls, including dextran sulfate (an attachment inhibitor), 3'-Azido-2'-3'-dideoxythymidine, or AZT (a reverse transcriptase inhibitor), are added to each assay. Individual assays are done in duplicate using a sister plate method.

The ability of a drug to inhibit viral replication or infectivity is expressed as the $EC_{50}$ of the drug, or the effective concentration that prevents 50% of viral replication. Methods described above to determine the infectivity of a virus are useful to determine the $EC_{50}$ of a drug.

The ability of a drug to kill cells is expressed as the $IC_{50}$, or the concentration of drug that inhibit cellular proliferation. Methods to determine the $IC_{50}$, of a drug are known to those of skill in the art and include determination of cell viability after incubation with a range of concentrations of the drug.

IX. Pharmaceutical Compositions of the Invention

The present invention provides pharmaceutical compositions which inhibit the replication of viruses and the growth of cancer cells. These pharmaceutical compositions comprise a prodrug of a base, nucleoside, or nucleotide and a pharmaceutically acceptable carrier. In one embodiment of the invention, the pharmaceutical compositions comprise prodrugs of cytosine and a pharmaceutically acceptable carrier. In another embodiment, the pharmaceutical compositions comprise a compound according to Formula I and a pharmaceutically acceptable carrier.

A pharmaceutical composition of the invention, or pharmaceutically acceptable addition salt or hydrate thereof, can be delivered to a patient using a wide variety of routes or modes of administration. Suitable routes of administration include, but are not limited to, oral, transdermal, transmucosal (such as intranasal or intravaginal), and parenteral administration, including intramuscular, subcutaneous and intravenous injections.

In an exemplary embodiment, the present invention provides a method of treating a viral disease or treating cancer by administering the compound orally.

A. Oral Administration

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the composition with a suitable solid phase excipient, optionally grinding the resulting mixture, and processing the mixture of granules, after adding suitable auxiliaries, if desired, to obtain tablets or dragee cores. Suitable excipients are, for example, calcium carbonate, calcium phosphate, polymers such as poly(ethylene oxide), fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, poly(ethylene oxide), and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

B. Parenteral Administration

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as cross-linked polyvinyl pyrrolidone, agar, or alginic acid or a salt thereof such as sodium alginate. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one embodiment, the transdermal delivery agent can be DMSO. In another embodiment, the transdermal delivery agent can be a transdermal patch. The compounds may be formulated, for example, with suitable polymeric or hydrophobic materials (e.g., as an emulsion in an acceptable oil) or ion exchange resins, or as sparingly soluble derivatives, for example, as a sparingly soluble salt.

Examples of aqueous solutions that can be used in formulations for transmucosal drug delivery include, e.g., water, saline, phosphate buffered saline, Hank's solution, Ringer's solution, dextrose/saline, glucose solutions and the like. The formulations can contain pharmaceutically acceptable auxiliary substances to enhance stability, deliverability or solubility, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

The choice of therapeutic agents that can be co-administered with the compounds of the invention will depend, in part, on the condition being treated. For example, when administered to a patient undergoing cancer treatment, the compounds may be administered in cocktails containing other bioactive agents, such as anti-cancer agents and/or supplementary potentiating agents. The compounds may also be administered in cocktails containing agents that treat the side-effects of radiation therapy, such as anti-emetics, radiation protectants, etc.

Other suitable bioactive agents include, for example, antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopoly-saccharide, macrophage activation factor), sub-units of bacteria (such as *Mycobacteria* and *Corynebacteria*), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, and β-lactam antibiotics (e.g., sulfazecin); hormones and steroids such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dimutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin, amantadine, vidarabine, and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon and heparin; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin Q penicillin V, ticarcillin rifampin and tetracycline; antiinflammatories such as diffinisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium. In certain preferred embodiments, the bioactive agent is a monoclonal antibody, such as a monoclonal antibody capable of binding to a melanoma antigen.

Frequency of administration of the therapeutic compositions described herein, as well as dosage, will vary from individual to individual, and may be readily established using standard techniques. Preferably, between 1-100 doses may be administered over a 52-week period. When treating a viral disease, a suitable dose is an amount of a compound that, when administered as described above, is capable of killing or limiting the infectivity of a virus. When treating cancer, a suitable dose is an amount of a compound that, when administered as described above, is capable of killing or slowing the growth of cancers or cancer cells. Those of skill in the art are aware of the routine experimentation that will produce an appropriate dosage range for a patient in need of treatment by oral administration or any other method of administration of a drug, e.g., intravenous administration or parenteral administration, for example. Those of skill are also aware that results provided by in vitro or in vivo experimental models can be used to extrapolate approximate dosages for a patient in need of treatment.

In general, an appropriate dosage and treatment regimen provides the pharmaceutical composition in an amount sufficient to provide therapeutic and/or prophylactic benefit. Such a response can be monitored by establishing an improved clinical outcome (e.g., longer viral disease-free survival or, for cancer patients, more frequent remissions or complete, partial, or longer disease-free survival) in treated patients as compared to non-treated patients.

X. Combination Therapies

The compounds of the present invention can be administered in combination with other known agents useful for the treatment of viral diseases such as HIV. In some embodiments, the combination of the compounds of the present invention and other antiviral agents can create a synergistic effect where the combination is more effective than either the compound or antiviral agent separately. In some embodiments, one or both of the compounds has enhanced activity.

A. Antiviral Agents for the Combination Therapies

Drugs useful in the combination therapies of the present invention are known antiviral agents for the treatment of HIV. Antiviral agents of the present invention include, but are not limited to, nucleoside/nucleotide reverse transcriptase inhibitors (NRTIs), non-nucleoside reverse transcriptase inhibitors (NNRTIs), protease inhibitors (PI), fusion inhibitors (FIs), integrase inhibitors, entry inhibitors, maturation inhibitors and immune-based therapeutic agents.

NRTIs useful in the present invention include, but are not limited to, abacavir (U.S. Pat. No. 5,034,934), didanosine, emtricitabine (U.S. Pat. No. 5,210,085), lamivudine (U.S. Pat. No. 5,034,934), stavudine (U.S. Pat. No. 4,978,655), tenofovir (U.S. Pat. No. 5,210,085), zalcitabine (U.S. Pat. No. 4,879,277), zidovudine (U.S. Pat. No. 4,724,232), elvucitabine from Achillion, amdoxovir from RFS Pharma and apricitabine from Avexa. In some embodiments, the compounds of the present invention are not used in combination with NRTI cytidine analogs such as emtricitabine, lamivudine and zalcitabine.

NNRTIs useful in the present invention include, but are not limited to, delavirdine (U.S. Pat. No. 5,563,142), efavirenz (U.S. Pat. No. 5,519,021), nevirapine (U.S. Pat. No. 5,366,972), etravirine from Tibotec and TMC-278 from Tibotec.

Protease inhibitors useful in the present invention include, but are not limited to, amprenavir (U.S. Pat. No. 5,585,397), atazanavir (U.S. Pat. No. 5,849,911), fosamprenavir (U.S. Pat. No. 6,436,989), indinavir (U.S. Pat. No. 5,413,999), lopinavir (U.S. Pat. No. 5,541,206), nelfinavir (U.S. Pat. No. 5,484,926), ritonavir (U.S. Pat. No. 5,541,206), saquinavir (U.S. Pat. No. 5,196,438), tipranavir (U.S. Pat. No. 5,852,195), darunavir (U.S. Pat. No. 5,843,946) and brecanaivir from Glaxo.

Fusion inhibitors useful in the present invention include, but are not limited to, enfuvirtide (U.S. Pat. No. 5,464,933).

Integrase inhibitors useful in the present invention include, but are not limited to, MK-0518 from Merck and GS-9137 from Gilead.

Entry inhibitors useful in the present invention include, but are not limited to, maraviroc, blocks CCR5 co-receptor, from Pfizer, vicriviroc, blocks CCR5 co-receptor, from Schering, CCR5 mAb004, an anti-CCR5 monoclonal antibody, from Human Genome Sciences and TNX-355, an anti-CD4 monoclonal antibody, from Tanox.

Maturation inhibitors useful in the present invention include, but are not limited to, bevirimat from Panacos.

Immune-based therapeutic agents useful in the present invention include, but are not limited to, Immunitin from HollisEden, IL-2 from Chiron (Novartis), Bay 50-4798 (a modified IL-2) from Bayer and IL-8.

B. Combination Formulations

Pharmaceutical formulations of combinations comprising the compounds of the present invention and additional known antiviral agents can be prepared separately or together in a pharmaceutical formulation. Pharmaceutical formulations of the combinations of the present invention can be prepared as described herein. The combination of the two pharmaceutical dosage forms may be packed as a single medical product or kit for use in the invention, or can be administered separately but in the same course of treatment.

Therapeutic formulations are prepared by any methods well known in the art of pharmacy. See, e.g., Gilman et al., eds., Goodman and Gilman's: The Pharmacological Bases of Therapeutics, 8th ed., Pergamon Press, 1990; and Remington's Pharmaceutical Sciences, 17th ed., Mack Publishing Co., Easton, P.a., 1990; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

In some embodiments, the present invention provides a pharmaceutical composition comprising a therapeutically effective amount of a compound of the present invention and an antiviral agent, for the treatment of HIV infection. In other embodiments, the antiviral agent is a member selected from the group consisting of nucleoside/nucleotide reverse transcriptase inhibitors (NRTIs), non-nucleoside reverse transcriptase inhibitors (NNRTIs), protease inhibitors (PI), fusion inhibitors (FIs), integrase inhibitors, entry inhibitors, maturation inhibitors and immune-based therapeutic agents.

In another embodiment, the present invention provides a method for treating HIV infection, the method comprising the step of administering to a subject in need of such treatment a therapeutically effective amount of a compound of the present invention and an antiviral agent. In still another embodiment, the antiviral agent is a member selected from the group consisting of nucleoside/nucleotide reverse transcriptase inhibitors (NRTIs), non-nucleoside reverse transcriptase inhibitors (NNRTIs), protease inhibitors (PI), fusion inhibitors (FIs), integrase inhibitors, entry inhibitors, maturation inhibitors and immune-based therapeutic agents. In yet another embodiment, the antiviral agent and the compound are admixed in a pharmaceutical composition. In still yet another embodiment, the antiviral agent and the compound are administered separately.

C. Timing of Administration

The components of the combination can be administered together or separately. The components of the combination can be administered simultaneously, during the same hour, day, week or month, or during the same therapy. The components of the combination or the combination thereof can be administered periodically, e.g. hourly, daily, weekly or biweekly, or monthly, depending on the patient's needs. Alternatively, the components of the combination or the combination can be administered several times a day, several times a week, several times a month or several times a year.

All references and patent publications referred to herein are hereby incorporated by reference herein. As can be appreciated from the disclosure provided above, the present invention has a wide variety of applications. Accordingly, the following examples are offered for illustration purposes and are not intended to be construed as a limitation on the invention in any way.

EXAMPLES

General

In the examples below, unless otherwise stated, temperatures are given in degrees Celsius (° C.); operations were carried out at room or ambient temperature, "rt," or "RT," (typically a range of from about 18-25° C.); evaporation of solvent was carried out using a rotary evaporator under reduced pressure (typically, 4.5-30 mm Hg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Unless otherwise specified, all solvents (HPLC grade) and reagents were purchased from suppliers and used without further purification. Reactions were conducted under a blanket of argon unless otherwise stated. Analytical thin layer chromatography (TLC) was performed on plates from EM Science (Silica Gel 60F$_{254}$, 0.25 mm thickness) using a (12:1:1:1) ethyl acetate:acetone:water:methanol mixture. Compounds were visualized under UV lamp (254 nM) or by developing with 3N H$_2$SO$_4$/0.5% cysteine solution followed by heating. Flash chromatography was done using silica gel from Whatman Inc. 60 Å silica gel (particle size 230-400 mesh). $^1$H NMR spectra were recorded on a Varian 300 machine at 300 MHz. LC MS analysis was performed on a ThermoFinnigan LCQ Advantage machine using a 0.01 M ammonium acetate:MeCN gradient and UV and ESI for detection. Melting points were recorded on a Electrothermal 1101D MEL-TEMP apparatus and were uncorrected.

Example 1

Preparation of N$^4$-alkyloxycarbonyl-2'-deoxy-5,6-dihydro-5-azacytidines 1.1 General Procedure β-2'-Deoxy-5,6-dihydro-5-azacytidine (40.2 g, 0.175 mol) was suspended in 850 mL of pyridine and cooled with ice. The mixture was treated with chlorotrimethylsilane (72 mL, 0.570 mol) and kept on ice for 40 min. Corresponding alkylchloroformate (0.350 mol) was added to the mixture, and the mixture was kept on ice for 2 hrs. The mixture was treated with methanol (200 mL) and evaporated under vacuum. The residue was taken into ethyl acetate (1 L) and washed with water (0.5 L). The extract was washed subsequently with saturated NaHCO$_3$ and saturated NaCl and dried over Na$_2$SO$_4$. The extract was evaporated and the residue was treated with triethylamine (80 mL) in methanol (800 mL) at room temperature for 10 hrs and evaporated. The residue was dissolved in chloroform and deposited on a silica gel column. The product was eluted with a 10:1 ethyl acetate:methanol mixture for the prodrugs containing C$_9$-C$_{16}$ alkyl chains and 5:1 ethyl acetate:methanol mixture for the prodrugs containing C$_5$-C$_8$ alkyl chains. Fractions containing the main product were combined, evaporated and recrystallized from ethyl acetate, methanol, isopropanol or isopropanol-ether mixtures.

1.2 Results

Analytical data for exemplary compounds of the invention are provided below.

1.2.a N$^4$-Amyloxycarbonyl-β-2'-deoxy-5,6-dihydro-5-azacytidine

The compound was obtained as a colorless solid using n-amylchloroformate, m.p. 75-78°, (37% yield). $^1$H NMR (300 MHz, DMSO-d$_6$) δ 0.858 (t, J=6.6 Hz, 3H, Me), 1.20-1.33 (m, 4H, (CH$_2$)$_2$), 1.50-1.58 (m, 2H, OCH$_2$CH$_2$), 1.80-1.87 (m, 1H, H-2'), 1.95-2.04 (m, 1H, H-2''), 3.32 (br s, water), 3.42 (t, J=4.8 Hz, 2H, H-5'), 3.60-3.64 (m, 1H, H-4'), 3.94 (t, J=6.8 Hz, 2H, OCH$_2$), 4.08-4.13 (m, 1H, H-3'), 4.55 (dd, J$_1$=18.4 Hz, J$_2$=10.4 Hz, 2H, 6-CH$_2$), 4.78 (t, J=5.2 Hz, 1H, OH-5'), 5.14 (d, J=4.4 Hz, 1H, OH-3'), 6.01 (dd, J=8.0 Hz, J$_2$=6.4 Hz, 1H, H-1'), 9.4 (br s, 1H, 5-NH), 10.1 (br s, 1H, NHCO). MS (ESI m/z) 345 (M+H)$^+$.

1.2b N$^4$-Hexyloxycarbonyl-β-2'-deoxy-5,6-dihydro-5-azacytidine

The compound was obtained as a colorless solid using n-hexylchloroformate, m.p. 138-139°, (41% yield). $^1$H NMR (300 MHz, DMSO-d$_6$) δ 0.858 (t, J=6.6 Hz, 3H, Me), 1.20-1.33 (m, 6H, (CH$_2$)$_3$), 1.50-1.58 (m, 2H, OCH$_2$CH$_2$), 1.80-1.88 (m, 1H, H-2'), 1.95-2.04 (m, 1H, H-2"), 3.32 (br s, water), 3.42 (t, J=4.4 Hz, 2H, H-5'), 3.60-3.64 (m, 1H, H-4'), 3.94 (t, J=6.8 Hz, 2H, OCH$_2$), 4.08-4.13 (m, 1H, H-3'), 4.55 (dd, J=18.4 Hz, J$_2$=10.4 Hz, 2H, 6-CH$_2$), 4.77 (br s, 1H, OH-5'), 5.14 (d, J=4.0 Hz, 1H, OH-3'), 6.01 (dd, J$_1$=8.0 Hz, J$_2$=6.4 Hz, 1H, H-1'), 9.4 (br s, 1H, 5-NH), 10.1 (br s, 1H, NHCO). MS (ESI m/z) 359 (M+H)$^+$.

1.2.c N$^4$-Heptyloxycarbonyl-β-2'-deoxy-5,6-dihydro-5-azacytidine

The compound was obtained as a colorless solid using n-heptylchloroformate, m.p. 126-127.7°, (85% yield). $^1$H NMR (300 MHz, DMSO-d$_6$) δ 0.857 (t, J=6.6 Hz, 3H, Me), 1.20-1.33 (m, 8H, (CH$_2$)$_4$), 1.50-1.58 (m, 2H, OCH$_2$CH$_2$), 1.80-1.88 (m, 1H, H-2'), 1.96-2.04 (m, 1H, H-2"), 3.31 (br s, water), 3.42 (d, J=4.4 Hz, 2H, H-5'), 3.60-3.64 (m, 1H, H-4'), 3.94 (t, J=6.8 Hz, 2H, OCH$_2$), 4.08-4.13 (m, 1H, H-3'), 4.56 (dd, J=19.2 Hz, J$_2$=10.8 Hz, 2H, 6-CH$_2$), 4.77 (br s, 1H, OH-5'), 5.14 (br s, 1H, OH-3'), 6.00 (dd, J$_1$=8.0 Hz, J$_2$=6.4 Hz, 1H, H-1'), 9.4 (br s, 1H, 5-NH), 10.1 (br s, 1H, NHCO). MS (ESI m/z) 373 (M+H)$^+$.

1.2.d N$^4$-Octyloxycarbonyl-β-2'-deoxy-5,6-dihydro-5-azacytidine

The compound was obtained as a colorless solid using n-octylchloroformate, m.p. 135-137°, (75% yield). $^1$H NMR (300 MHz, DMSO-d$_6$) δ 0.856 (t, J=6.0 Hz, 3H, Me), 1.20-1.31 (m, 10H, (CH$_2$)$_5$), 1.50-1.58 (m, 2H, OCH$_2$CH$_2$), 1.80-1.88 (m, 1H, H-2'), 1.95-2.04 (m, 1H, H-2"), 3.32 (br s, water), 3.43 (d, J=4.4 Hz, 2H, H-5'), 3.60-3.64 (m, 1H, H-4'), 3.94 (t, J=6.8 Hz, 2H, OCH$_2$), 4.08-4.13 (m, 1H, H-3'), 4.55 (dd, J$_3$=18.8 Hz, J$_2$=10.8 Hz, 2H, 6-CH$_2$), 4.78 (br s, 1H, OH-5'), 5.14 (br s, 1H, OH-3'), 6.01 (dd, J$_1$=8.0 Hz, J$_2$=6.4 Hz, 1H, H-1'), 9.4 (br s, 1H, 5-NH), 10.0 (br s, 1H, NHCO). MS (ESI m/z) 387 (M+H)$^+$.

1.2.e N$^4$-(2-Ethylhexyl)oxycarbonyl-β-2'-deoxy-5,6-dihydro-5-azacytidine

The compound was obtained as a colorless solid using (2-ethylhexyl)chloroformate, m.p. 118-120°, (55% yield). $^1$H NMR (300 MHz, DMSO-d$_6$) δ 0.82-0.89 (m, 6H, Me), 1.22-1.33 (m, 8H, CH$_2$), 1.46-1.54 (m, 1H, CH), 1.80-1.87 (m, 1H, H-2'), 1.95-2.04 (m, 1H, H-2"), 3.32 (br s, water), 3.42 (t, J=5.0 Hz, 2H, H-5'), 3.60-3.64 (m, 1H, H-4'), 3.84-3.90 (m, 2H, OCH$_2$), 4.08-4.13 (m, 1H, H-3'), 4.56 (dd, J$_3$=19.0 Hz, J$_2$=10.6 Hz, 2H, 6-CH$_2$), 4.77 (t, J=5.4 Hz, 1H, OH-5'), 5.14 (d, J=4.0 Hz, 1H, OH-3'), 6.01 (dd, J$_1$=8.0 Hz, J$_2$=6.0 Hz, 1H, H-1'), 9.4 (br s, 1H, 5-NH), 10.1 (br s, 1H, NHCO). MS (ESI m/z) 387 (M+H)$^+$.

1.2.f N$^4$-Nonyloxycarbonyl-β-2'-deoxy-5,6-dihydro-5-azacytidine

The compound was obtained as a colorless solid using n-nonylchloroformate, m.p. 137-138.4°, (75% yield). $^1$H NMR (300 MHz, DMSO-d$_6$) δ 0.855 (t, J=6.0 Hz, 3H, Me), 1.20-1.31 (m, 12H, (CH$_2$)$_6$), 1.50-1.58 (m, 2H, OCH$_2$CH$_2$), 1.80-1.88 (m, 1H, H-2'), 1.95-2.04 (m, 1H, H-2"), 3.32 (br s, water), 3.42 (d, J=4.4 Hz, 2H, H-5'), 3.60-3.64 (m, 1H, H-4'), 3.94 (t, J=6.8 Hz, 2H, OCH$_2$), 4.08-4.13 (m, 1H, H-3'), 4.55 (dd, J$_3$=10.8 Hz, J$_2$=18.8 Hz, 2H, 6-CH$_2$), 4.78 (br s, 1H, OH-5'), 5.14 (br s, 1H, OH-3'), 6.00 (dd, J$_1$=8.0 Hz, J$_2$=6.4 Hz, 1H, H-1'), 9.4 (br s, 1H, 5-NH), 10.0 (br s, 1H, NHCO). MS (ESI m/z) 401 (M+H)$^+$.

1.2.g N$^4$-Decyloxycarbonyl-β-2'-deoxy-5,6-dihydro-5-azacytidine

The compound was obtained as a colorless solid using n-decylchloroformate, m.p. 124-126°, (86% yield). $^1$H NMR (300 MHz, DMSO-d$_6$) δ 0.853 (t, J=6.0 Hz, 3H, Me), 1.20-1.31 (m, 14H, (CH$_2$)$_7$), 1.50-1.58 (m, 2H, OCH$_2$CH$_2$), 1.80-1.87 (m, 1H, H-2'), 1.95-2.04 (m, 1H, H-2"), 3.32 (br s, water), 3.42 (t, J=4.8 Hz, 2H, H-5'), 3.60-3.64 (m, 1H, H-4'), 3.94 (t, J=6.8 Hz, 2H, OCH$_2$), 4.08-4.13 (m, 1H, H-3'), 4.55 (dd, J$_1$=18.4 Hz, J$_2$=10.4 Hz, 2H, 6-CH$_2$), 4.78 (t, J=4.8 Hz, 1H, OH-5'), 5.14 (d, J=4.4 Hz, 1H, OH-3'), 6.01 (dd, J$_1$=8.0 Hz, J$_2$=6.4 Hz, 1H, H-1'), 9.4 (br s, 1H, 5-NH), 10.0 (br s, 1H, NHCO). MS (ESI m/z) 415 (M+H)$^+$.

1.2.h N$^4$-Dodecyloxycarbonyl-β-2'-deoxy-5,6-dihydro-5-azacytidine

The compound was obtained as a colorless solid using n-dodecylchloroformate, m.p. 138-140°, (76% yield). $^1$H NMR (300 MHz, DMSO-d$_6$) δ 0.853 (t, J=7.0 Hz, 3H, Me), 1.20-1.31 (m, 18H, (CH$_2$)$_9$), 1.50-1.60 (m, 2H, OCH$_2$CH$_2$), 1.80-1.87 (m, 1H, H-2'), 1.95-2.04 (m, 1H, H-2"), 3.31 (br s, water), 3.42 (t, J=5.2 Hz, 2H, H-5'), 3.60-3.64 (m, 1H, H-4'), 3.94 (t, J=6.8 Hz, 2H, OCH$_2$), 4.08-4.13 (m, 1H, H-3'), 4.55 (dd, J$_1$=18.4 Hz, J$_2$=10.4 Hz, 2H, 6-CH$_2$), 4.78 (t, J=4.8 Hz, 1H, OH-5'), 5.14 (d, J=4.4 Hz, 1H, OH-3'), 6.01 (dd, J$_1$=8.0 Hz, J$_2$=6.4 Hz, 1H, H-1'), 9.4 (br s, 1H, 5-NH), 10.0 (br s, 1H, NHCO). MS (ESI m/z) 443 (M+H)$^+$.

1.2.i N$^4$-Hexadecyloxycarbonyl-β-2'-dihydro-5-azacytidine

The compound was obtained as a colorless solid using n-hexadecylchloroformate, m.p. 119-123°, (73% yield). $^1$H NMR (300 MHz, DMSO-d$_6$) δ 0.853 (t, J=6.0 Hz, 3H, Me), 1.20-1.31 (m, 26H, (CH$_2$)$_{13}$), 1.50-1.58 (m, 2H, OCH$_2$CH$_2$), 1.80-1.88 (m, 1H, H-2'), 1.95-2.04 (m, 1H, H-2"), 3.31 (br s, water), 3.42 (t, J=4.8 Hz, 2H, H-5'), 3.59-3.64 (m, 1H, H-4'), 3.94 (t, J=6.4 Hz, 2H, OCH$_2$), 4.08-4.13 (m, 1H, H-3'), 4.56 (dd, J$_3$=18.8 Hz, J$_2$=10.8 Hz, 2H, 6-CH$_2$), 4.78 (t, J=5.2 Hz, 1H, OH-5'), 5.14 (d, J=4.0 Hz, 1H, OH-3'), 6.01 (dd, J$_1$=7.6 Hz, J$_2$=6.8 Hz, 1H, H-1'), 9.4 (br s, 1H, 5-NH), 10.0 (br s, 1H, NHCO). MS (ESI m/z) 499 (M+H)$^+$.

1.2.j N$^4$-Heptyloxycarbonyl-α-2'-deoxy-5,6-dihydro-5-azacytidine

The compound was obtained as a colorless solid using α-2'-deoxy-5,6-dihydro-5-azacytidine and n-heptylchloroformate, m.p. 77-78°, (30% yield). $^1$H NMR (300 MHz, DMSO-d$_6$) δ 0.857 (t, J=6.8 Hz, 3H, Me), 1.20-1.33 (m, 8H, ($CH_2)_4$), 1.50-1.58 (m, 2H, $OCH_2CH_2$), 1.68-1.76 (m, 1H, H-2'), 2.38-2.47 (m, 1H, H-2"), 3.31 (br s, water), 3.33-3.40 (m, 2H, H-5'), 3.82-3.87 (m, 1H, H-4'), 3.94 (t, J=6.6 Hz, 2H, $OCH_2$), 4.11-4.16 (m, 1H, H-3'), 4.60 (d, J=11.2 Hz, 1H, 6-$CH_a$), 4.75 (t, J=5.6 Hz, 1H, OH-5'), 4.77 (d, J=11.2 Hz, 1H, 6-$CH_b$), 5.24 (d, J=3.6 Hz, 1H, OH-3'), 5.97 (dd, $J_1$=8.0 Hz, $J_2$=4.8 Hz, 1H, H-1'), 9.4 (br s, 1H, 5-NH), 9.9 (br s, 1H, NHCO). MS (ESI m/z) 373 (M+H)$^+$.

Example 2

Experimental Conditions for the Bioavailability Studies of the Compounds in Rats This study tested the bioavailability of different test compounds in rats, by oral gavage administration, at prescribed dose levels.

The animals tested in this study were *Rattus norvegicus*, CD strain, from Charles River Canada (Montreal, Canada). Six males were included in each test group. Their weight ranged from 200 to 250 grams before fasting. The weight variation in animals at the initiation of the study did not exceed plus or minus 20% of the mean weight.

Rats were individually housed in Nalgene rat cages with stainless steel covers. The animal room environment was controlled and monitored daily. The temperature ranged from 18 to 26° C. and the relative humidity ranged from 30%-70%. The photocycle was 12 hours light and 12 hours dark. All animals were submitted to a general physical examination and only those found healthy were admitted for the study. All selected animals were given two days to adjust to laboratory conditions before the study began. Teklad rodent Diet and water were constantly available to the rats throughout the acclimatization and study periods.

Forty-eight hours prior to the initiation of the study, animals were randomly selected and two subsets of 3 male rats per group were formed. Due to the large volume of blood taken, collections will be done by alternating timepoints between subsets.

All animals were fasted for twelve hours prior to the initiation of the study. At the study initiation, respective groups of rats received the compound of the invention by oral gavage at a dose of 4.0 mL/kg.

Blood was collected from the orbital sinus of animals from each group at thirty minutes and at 1, 2, 4, and 12 hours after dosing. At each blood collection time point, three rats per group were bled.

Example 3

Pharmacokinetic Data for the Compounds of the Invention in Rats

DHAdC (5,6-dihydro-5-aza-2'-deoxycytidine) and the prodrugs $C_7$-DHAdC($N^4$-heptyloxycarbonyl-DHAdC) and $C_9$-DHAdC($N^4$-nonyloxycarbonyl-DHAdC) were administered to rats under the conditions described in Example 2. Oral and IV dosages of DHAdC, as well as oral dosages of prodrugs $C_7$-DHAdC and $C_9$-DHAdC were recorded. The rats were administered 100 mg/kg DHAdC or DHAdC equivalent in the case of prodrugs. The maximum concentration ($C_{max}$), clearance (AUC∞), half-life ($T_{1/2}$), and % Oral Bioavailability were recorded and are presented in Table 1:

TABLE 1

|  | DHAdC (IV) | DHAdC (oral) | $C_7$-DHAdC (oral) | $C_9$-DHAdC (oral) |
|---|---|---|---|---|
| $C_{max}$ (ng/mL) | 40,034 | 1,858 | 5,577 | 5,550 |
| AUC∞ (ng-hr/mL) | 74,975.1 | 8,538 | 32,101 | 26,472 |
| $T_{1/2}$ (hr) | 1.8 | 0.8 | 3.9 | 3.6 |
| Oral bioavailability (%) | N/A | 11 | 43 | 35 |

Example 4

Experimental Conditions for the Bioavailability Studies of the Compounds in Dogs This study tested the bioavailability of different test compounds in dogs, by intravenous or oral gavage administration, at prescribed dose levels.

The animals tested in this study were *Canis familiaris*, from Harlan Sprague Dawley (Indianapolis, Ind.). Four dogs (2 males and 2 females), with an average age of seven months, were included in each test group. The dogs were identified by ear tattoos, and given a fourteen day acclimatization period prior to the commencement of testing.

Dogs were group housed but separated by sex. The animal room environment was controlled and monitored daily. The temperature ranged from 18 to 29° C. and the relative humidity ranged from 30%-70%. The photocycle was 12 hours light and 12 hours dark. All animals were submitted to a general physical examination and only those found healthy were admitted for the study. All selected animals were given two days to adjust to laboratory conditions before the study began. Teklad Dog Diet was fed twice daily and water was constantly available to the dogs throughout the acclimatization and study periods.

Twenty-four hours prior to the initiation of the study, animals were randomly selected into two groups with 1 male and 1 female in each group. At the study initiation, the respective groups of dogs then received a compound of the invention by intravenous injection or oral gavage administration at 0.5 mL/kg.

Blood was collected from the v. cephalica antebrachii of each of the two animals prior to study initiation, at thirty minutes and at 1, 2, 4, and 12 hours after dosing.

Example 5

Pharmacokinetic Data for the Compounds of the Invention in Dogs

DHAdC (5,6-dihydro-5-aza-2'-deoxycytidine) and the prodrugs $C_7$-DHAdC(N-heptyloxycarbonyl-DHAdC), $C_8$-DHAdC($N^4$-octyloxycarbonyl-DHAdC), and $C_9$-DHAdC ($N^4$-nonyloxycarbonyl-DHAdC) were administered to dogs under the conditions described in Example 4. IV dosages of DHAdC, as well as oral dosages of prodrugs $C_7$-DHAdC, $C_8$-DHAdC, and $C_9$-DHAdC were recorded. The dogs were administered 50 mg/kg DHAdC or DHAdC equivalent in the case of prodrugs. The maximum concentration ($C_{max}$), clearance (AUC∞), half-life ($T_{1/2}$), and % Oral Bioavailability were recorded and are presented in Table 2:

TABLE 2

| | DHAdC (IV) | $C_7$-DHAdC (oral) | $C_8$-DHAdC (oral) | $C_9$-DHAdC (oral) |
|---|---|---|---|---|
| $C_{max}$ (ng/mL) | 76,333 | 11,282 | 5,172 | 8,932 |
| AUC∞ (ng-hr/mL) | 156,058 | 59,377 | 17,845 | 54,540 |
| $T_{1/2}$ (hr) | 2.1 | 2.1 | 2.8 | 2.2 |
| Oral bioavailability (%) | N/A | 51 | 11 | 36 |

Example 6

Experimental Conditions for the Lipophilicity Study

This study tested the lipophilicity of different test compounds.

The compounds were first dissolved in a 60% methanol/40% water (v/v) solution containing 1% DMSO and brought to a concentration of 100 μM. The optimal detection wavelength was determined and calibration studies were performed with the solution. After calibration, the compounds were placed into n-octanol-PBS buffer at pH 7.4 at RT. The mixture was shaken and allowed to equilibrate for 60 minutes. The amount of compound in the PBS buffer phase was then determined by HPLC/UV-Vis. The amount of compound in n-octanol was determined by subtracting the original amount from the amount in the PBS buffer phase. This experiment was conducted for three samples. These three samples were then each corrected for volume and the results were averaged. Log D was calculated as the $Log_{10}$ of the amount of compound in the n-octanol phase divided by the amount of compound in the buffer phase.

Example 7

Lipophilicity Data for the Compounds of the Invention

Lipophilicity is a major structural factor that influences the pharmacokinetic and pharmacodynamic behavior of compounds. In this assay, prodrugs $C_7$-DHAdC, $C_8$-DHAdC, and $C_9$-DHAdC were partitioned between n-octanol and phosphate buffered saline (PBS). The log D values of the prodrugs are recorded in Table 3:

TABLE 3

| Compound I.D. Test Concentration (uM) | log D n-Octanol PBS pH 7.4 100 um |
|---|---|
| $C_7$-DHAdC | 2.04 |
| $C_8$-DHAdC | 2.56 |
| $C_9$-DHAdC | 3.16 |

A value between 2.0 and 2.5 might be considered optimal.

What is claimed:

1. A pharmaceutical composition comprising a therapeutically effective amount of a compound of Formula I:

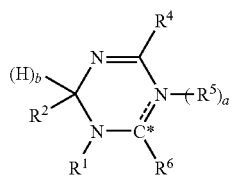

(I)

wherein
a is either 0 or 1;
b is either 0 or 1;
the dashed line represents a double bond between C* and N when a is 0;
$R^1$ is a structure according to Formula II:

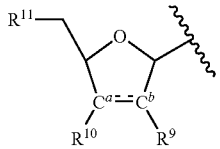

(II)

wherein
the dashed line represents a double bond between $C^a$ and $C^b$;
$R^9$, $R^{10}$ and $R^{11}$ members independently selected from H, —OH, —$OR^{12}$, —$NH_2$, —$NO_2$, —$SO_2NH_2$, $N_3$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
$R^2$ is a member selected from (=O) and $NR^7R^8$, such that when $R^2$ is (=O), b is 0, and when $R^2$ is $NR^7R^8$, b is 1;
$R^4$ is a member selected from H, halogen, $OR^3$, $NR^7R^8$, nitrile, and substituted and unsubstituted ($C_1$-$C_5$)alkyl;
$R^6$ is a member selected from H, halogen, substituted or unsubstituted O-alkyl, $NR^3R^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
$R^7$, $R^8$ and $R^5$ are members independently selected from H, $OR^3$, $NR^3R^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
$R^3$ is independently selected from H, substituted or unsubstituted alkyl and substituted or unsubstituted acyl;
wherein $R^7$ and $R^8$ together with the nitrogen to which they are joined optionally form a substituted or unsubstituted 5- to 7-membered ring;
wherein $R^8$ and $R^5$ together with the atoms to which they are joined optionally form a substituted or unsubstituted 5- to 7-membered ring;
wherein $R^5$ and $R^6$ together with the atoms to which they are joined optionally form a substituted or unsubstituted 5- to 7-membered ring;
wherein $R^{12}$ is selected from an amino acid and a peptide comprising between 2 and 5 amino acids;
wherein $R^9$ and $R^{10}$ together with the atoms to which they are joined optionally form a substituted or unsubstituted 5- to 7-membered ring;
wherein $R^{10}$ and $R^{11}$ together with the atoms to which they are joined optionally form a substituted or unsubstituted 5- to 7-membered ring; and
wherein at least one member selected from $R^3$, $R^5$, $R^7$, and $R^8$, alone or together with the atom to which it is covalently bonded, is selected from carbamate and urea linkers; and
an antiviral agent, for treatment of HIV infection.

2. The composition of claim 1, wherein the antiviral agent is a member selected from the group consisting of nucleoside/ nucleotide reverse transcriptase inhibitors (NRTIs), non-nucleoside reverse transcriptase inhibitors (NNRTIs), protease inhibitors (PI), fusion inhibitors (FIs), integrase inhibitors, entry inhibitors, maturation inhibitors and immune-based therapeutic agents.

3. A method for treating HIV infection, the method comprising the step of administering to a subject in need of such treatment a therapeutically effective amount of a compound of Formula I:

(I)

wherein
a is either 0 or 1;
b is either 0 or 1;
the dashed line represents a double bond between C* and N when a is 0;
$R^1$ is a structure according to Formula II:

(II)

wherein
the dashed line represents a double bond between $C^a$ and $C^b$;
$R^9$, $R^{10}$ and $R^{11}$ are members independently selected from H, —OH, —OR, —NH$_2$, —NO$_2$, —SO$_2$NH$_2$, N$_3$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
$R^2$ is a member selected from (=O) and NR$^7$R$^8$, such that when $R^2$ is (=O), b is 0, and when $R^2$ is NR$^7$R$^8$, b is 1;
$R^4$ is a member selected from H, halogen, OR$^3$, NR$^7$R$^8$, nitrile, and substituted and unsubstituted (C$_1$-C$_5$)alkyl;
$R^6$ is a member selected from H, halogen, substituted or unsubstituted O-alkyl, NR$^3$R$^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
$R^7$, $R^8$ and $R^5$ are members independently selected from H, OR$^3$, NR$^3$R$^3$, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
$R^3$ is independently selected from H, substituted or unsubstituted alkyl and substituted or unsubstituted acyl;
wherein $R^7$ and $R^8$ together with the nitrogen to which they are joined optionally form a substituted or unsubstituted 5- to 7-membered ring;
wherein $R^8$ and $R^5$ together with the atoms to which they are joined optionally form a substituted or unsubstituted 5- to 7-membered ring;
wherein $R^5$ and $R^6$ together with the atoms to which they are joined optionally form a substituted or unsubstituted 5- to 7-membered ring;
wherein $R^{12}$ is selected from an amino acid and a peptide comprising between 2 and 5 amino acids;
wherein $R^9$ and $R^{10}$ together with the atoms to which they are joined optionally form a substituted or unsubstituted 5- to 7-membered ring;
wherein $R^{10}$ and $R^{11}$ together with the atoms to which they are joined optionally form a substituted or unsubstituted 5- to 7-membered ring; and
wherein at least one member selected from $R^3$, $R^5$, $R^7$, and $R^8$, alone or together with the atom to which it is covalently bonded, is selected from carbamate and urea linkers; and an antiviral agent.

4. The method of claim 3, wherein the antiviral agent is a member selected from the group consisting of nucleoside/nucleotide reverse transcriptase inhibitors (NRTIs), non-nucleoside reverse transcriptase inhibitors (NNRTIs), protease inhibitors (PI), fusion inhibitors (FIs), integrase inhibitors, entry inhibitors, maturation inhibitors and immune-based therapeutic agents.

5. The method of claim 3, wherein the antiviral agent and the compound are admixed in a pharmaceutical composition.

6. The method of claim 3, wherein the antiviral agent and the compound are administered separately.

7. The method of claim 3, wherein said compound has the structure:

8. The composition of claim 1, wherein $R^2$ is selected from (=O), —NH$_2$, and —NHOH.

9. The composition of claim 1, wherein $R^4$ is selected from F, CN, —CCH, —CCMe, and CH$_3$.

10. The composition of claim 1, wherein $R^1$ comprises a hydroxyl moiety.

11. The composition of claim 1, wherein $R^9$, $R^{10}$ and $R^{11}$ are members independently selected from H, OH, (R$^{13}$)$_3$SiO—, and a structure according to Formula III:

(III)

wherein each $R^{13}$ is independently selected from substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted acyl, substituted or unsubstituted aryl, and substituted or unsubstituted heteroaryl;
wherein more than one $R^{13}$ together with the atoms to which they are joined optionally form a substituted or unsubstituted 5- to 7-membered ring; and wherein $R^{16}$, $R^{17}$, and $R^{18}$ are independently selected from substituted and unsubstituted alkyl.

12. The composition of claim 11, wherein $R^{16}$, $R^{17}$ and $R^{18}$ are ethyl.

13. The composition of claim 1, wherein $R^3$, $R^5$, $R^7$, and $R^8$ are independently selected from H and a structure according to Formula IV:

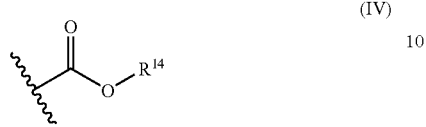

(IV)

wherein $R^{14}$ is selected from substituted or unsubstituted alkyl, substituted or unsubstituted heteroalkyl, substituted or unsubstituted cycloalkyl, substituted or unsubstituted heterocycloalkyl, substituted or unsubstituted acyl, substituted or unsubstituted aryl, substituted or unsubstituted heteroaryl, an amino acid, and a peptide comprising between 2 and 5 amino acids;

wherein if $R^8$ is a structure according to Formula IV, then $R^7$ is H.

14. The composition of claim 1, wherein $R^3$, $R^5$, $R^7$, and $R^8$ are independently selected from H and a structure according to Formula V:

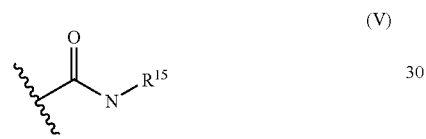

(V)

wherein $R^{15}$ is selected from substituted or unsubstituted alkyl, substituted or unsubstituted heteroalkyl, substituted or unsubstituted cycloalkyl, substituted or unsubstituted heterocycloalkyl, substituted or unsubstituted acyl, substituted or unsubstituted aryl, substituted or unsubstituted heteroaryl, an amino acid, and a peptide comprising between 2 and 5 amino acids;

wherein if $R^8$ is a structure according to Formula V, then $R^7$ is H.

15. The composition of claim 13, wherein $R^{14}$ is selected from substituted or unsubstituted $(C_4\text{-}C_{12})$alkyl, benzyl, 2-nitro-furanyl, retinol, α-tocopherol, calciferol, vitamin K, cholesterol,

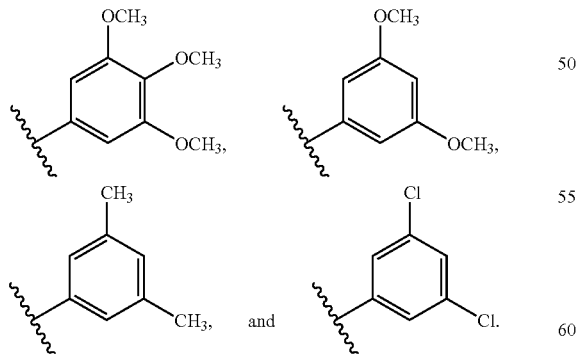

16. The composition of claim 14, wherein $R^{15}$ is selected from substituted or unsubstituted $(C_4\text{-}C_{12})$alkyl, benzyl, 2-nitro-furanyl, retinol, α-tocopherol, calciferol, vitamin K, cholesterol,

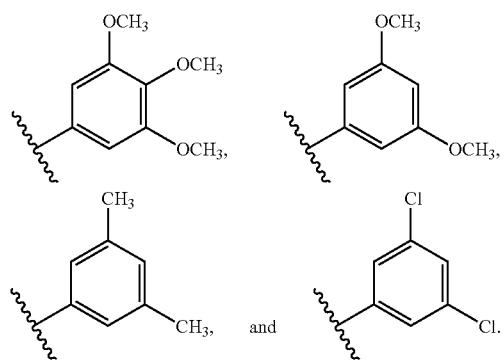

17. The composition of claim 15, wherein $R^{14}$ is unsubstituted $(C_6\text{-}C_{10})$alkyl.

18. The composition of claim 16, wherein $R^{15}$ is unsubstituted $(C_6\text{-}C_{10})$alkyl.

19. The composition of claim 13, wherein $R^2$ is selected from (=O), —NH$_2$, and —NHOH.

20. The composition of claim 14, wherein $R^2$ is selected from (=O), —NH$_2$, and —NHOH.

21. The composition of claim 15, wherein
$R^2$ is selected from (=O), —NH$_2$, and —NHOH; and
$R^4$ is selected from —F, —CN, —CCH, —CCMe, and —CH$_3$.

22. The composition of claim 16, wherein
$R^2$ is selected from (=O), —NH$_2$, and —NHOH; and
$R^4$ is selected from —F, —CN, —CCH, —CCMe, and —CH$_3$.

23. The composition of claim 1, wherein $R^4$ is $NR^7R^8$.

24. The composition of claim 23, wherein $R^7$ and $R^8$ are independently selected from H and a structure according to Formula IV:

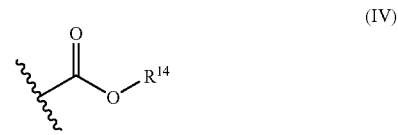

(IV)

wherein $R^{14}$ is selected from substituted or unsubstituted alkyl, substituted or unsubstituted heteroalkyl, substituted or unsubstituted cycloalkyl, substituted or unsubstituted heterocycloalkyl, substituted or unsubstituted acyl, substituted or unsubstituted aryl, substituted or unsubstituted heteroaryl, an amino acid, and a peptide comprising between 2 and 5 amino acids;

wherein if $R^8$ is a structure according to Formula IV, then $R^7$ is H.

25. The composition of claim 1, wherein said compound has the structure:

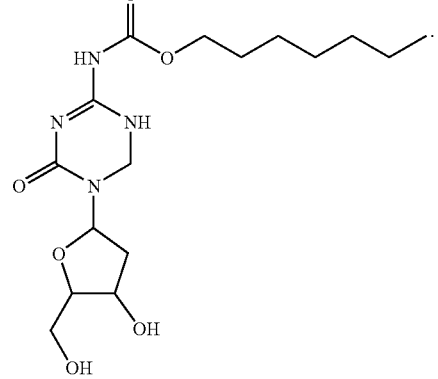

* * * * *